US009907838B2

(12) United States Patent
Kim

(10) Patent No.: US 9,907,838 B2
(45) Date of Patent: Mar. 6, 2018

(54) COMPOSITION AND METHODS FOR TREATING ISCHEMIC DAMAGE

(71) Applicants: GEMVAX & KAEL CO., LTD., Daejeon (KR); Sang Jae Kim, Seoul (KR)

(72) Inventor: Sang Jae Kim, Seoul (KR)

(73) Assignee: GEMVAX & KAEL CO., LTD., Daejeon (KR)

( * ) Notice: Subject to any disclaimer, the term of this patent is extended or adjusted under 35 U.S.C. 154(b) by 0 days.

(21) Appl. No.: 14/785,274

(22) PCT Filed: Apr. 18, 2014

(86) PCT No.: PCT/KR2014/003425
§ 371 (c)(1),
(2) Date: Oct. 16, 2015

(87) PCT Pub. No.: WO2014/171792
PCT Pub. Date: Oct. 23, 2014

(65) Prior Publication Data
US 2016/0082089 A1   Mar. 24, 2016

(30) Foreign Application Priority Data
Apr. 19, 2013   (KR) .................. 10-2013-0043636

(51) Int. Cl.
*A61K 38/45* (2006.01)
*A61K 38/10* (2006.01)
*C12N 9/12* (2006.01)
*A23L 29/00* (2016.01)

(52) U.S. Cl.
CPC .............. *A61K 38/45* (2013.01); *A23L 29/06* (2016.08); *A61K 38/10* (2013.01); *C12N 9/1276* (2013.01); *A23V 2002/00* (2013.01); *C12Y 207/07049* (2013.01)

(58) Field of Classification Search
None
See application file for complete search history.

(56) References Cited

U.S. PATENT DOCUMENTS

| | | | |
|---|---|---|---|
| 6,967,211 B2 | 11/2005 | Inoue | |
| 7,030,211 B1 * | 4/2006 | Gaudernack | ........... A61K 38/45 424/184.1 |
| 7,786,084 B2 * | 8/2010 | Benner | ................. A61K 38/24 514/21.7 |
| 7,794,723 B2 | 9/2010 | Gaudernack et al. | |
| 8,828,403 B2 | 9/2014 | Filaci et al. | |
| 8,933,197 B2 | 1/2015 | Bogin et al. | |
| 9,023,987 B2 | 5/2015 | Chung et al. | |
| 2003/0027769 A1 | 2/2003 | Scialdone et al. | |
| 2003/0143228 A1 | 7/2003 | Chen et al. | |
| 2006/0106196 A1 | 5/2006 | Gaudernack et al. | |
| 2007/0190561 A1 | 8/2007 | Morin et al. | |
| 2009/0136917 A1 | 5/2009 | Szalay et al. | |
| 2009/0186802 A1 | 7/2009 | Alluis et al. | |
| 2011/0135692 A1 | 6/2011 | Filaci et al. | |
| 2011/0150873 A1 | 6/2011 | Grainger | |
| 2011/0183925 A1 | 7/2011 | Sato et al. | |
| 2012/0065124 A1 | 3/2012 | Morishita et al. | |
| 2012/0208755 A1 | 8/2012 | Leung | |
| 2013/0129760 A1 | 5/2013 | Gaudernack et al. | |
| 2013/0230591 A1 | 9/2013 | Fellous et al. | |
| 2015/0099692 A1 | 4/2015 | Kim et al. | |
| 2015/0175978 A1 | 6/2015 | Kim | |
| 2015/0307859 A1 | 10/2015 | Kim | |
| 2015/0343095 A1 | 12/2015 | Kim | |
| 2015/0353903 A1 | 12/2015 | Kim | |
| 2016/0002613 A1 | 1/2016 | Kim | |
| 2016/0008438 A1 | 1/2016 | Kim | |
| 2016/0082089 A1 | 3/2016 | Kim | |
| 2016/0120966 A1 | 5/2016 | Kim | |
| 2016/0137695 A1 | 5/2016 | Kim | |
| 2016/0151512 A1 | 6/2016 | Kim | |
| 2016/0250279 A1 | 9/2016 | Kim | |

(Continued)

FOREIGN PATENT DOCUMENTS

| | | |
|---|---|---|
| EP | 1020190 A3 | 10/2000 |
| EP | 1093381 B2 | 7/2009 |
| EP | 1817337 B1 | 1/2011 |

(Continued)

OTHER PUBLICATIONS

Priya et al. (Tissue Engin. Part B, vol. 14, No. 1, pp. 105-118, 2008).*
Westin et al. (Antioxidants & Redox Signaling, vol. 14, No. 6, 2011, pp. 985-997).*
Dementia from Merck Manual, accessed on Jul. 29, 2009, pp. 1-17.
International Preliminary Report on Patentability for International Application No. PCT/KR2014/003425, The International Bureau of WIPO, Switzerland, dated Oct. 20, 2015, 14 pages.
International Preliminary Report on Patentability for International Application No. PCT/KR2014/005508, The International Bureau of WIPO, Switzerland, dated Jan. 5, 2016, 14 pages.

(Continued)

*Primary Examiner* — Hope Robinson
(74) *Attorney, Agent, or Firm* — Sterne, Kessler, Goldstein & Fox P.L.L.C.

(57) ABSTRACT

The present disclosure relates to a composition for treating and preventing an ischemic injury. More particularly, it relates to a composition containing a peptide derived from a telomerase, which is effective in treating and preventing an ischemic injury. The peptide according to the present disclosure, a peptide having 80% or more sequence identity with the amino acid sequence of the peptide or a peptide which is a fragment thereof, has a superior effect of treating and preventing an ischemic injury. Accordingly, a composition containing the peptide may be effectively used for an ischemic injury, particularly for an ischemic-reperfusion injury.

16 Claims, 13 Drawing Sheets

(56) References Cited

U.S. PATENT DOCUMENTS

2016/0296604 A1 10/2016 Kim

FOREIGN PATENT DOCUMENTS

| | | |
|---|---|---|
| JP | 2010252810 A | 11/2010 |
| JP | 5577472 B2 | 8/2014 |
| KR | 20010012613 A | 2/2001 |
| KR | 20010020601 A | 3/2001 |
| KR | 20040015087 A | 2/2004 |
| KR | 20040045400 A | 6/2004 |
| KR | 20040107492 A | 12/2004 |
| KR | 20050020987 A | 3/2005 |
| KR | 20050040517 A | 5/2005 |
| KR | 20060109903 A | 10/2006 |
| KR | 20070083218 A | 8/2007 |
| KR | 20080084818 A | 9/2008 |
| KR | 20090033878 A | 4/2009 |
| KR | 20090103957 A | 10/2009 |
| KR | 20100058541 A | 6/2010 |
| KR | 20100085527 A | 7/2010 |
| KR | 20110057049 A | 5/2011 |
| KR | 20110060940 A | 6/2011 |
| KR | 20110062943 A | 6/2011 |
| KR | 20110130943 A | 12/2011 |
| KR | 20120018188 A | 2/2012 |
| KR | 20120026408 A | 3/2012 |
| KR | 20120087885 A | 8/2012 |
| WO | WO-0002581 A1 | 1/2000 |
| WO | WO-2010003520 A2 | 1/2010 |
| WO | WO-2010012850 A1 | 2/2010 |
| WO | WO-2011101173 A1 | 8/2011 |
| WO | WO-2011150494 A1 | 12/2011 |
| WO | WO-2013100500 A1 | 7/2013 |
| WO | WO-2013118899 A1 | 8/2013 |
| WO | WO-2013135266 A1 | 9/2013 |
| WO | WO-2013167574 A1 | 11/2013 |
| WO | WO-2013169060 A1 | 11/2013 |
| WO | WO-2013169067 A1 | 11/2013 |
| WO | WO-2013169077 A1 | 11/2013 |
| WO | WO-2014010971 A1 | 1/2014 |
| WO | WO-2014046478 A1 | 3/2014 |
| WO | WO-2014046481 A1 | 3/2014 |
| WO | WO-2014046490 A1 | 3/2014 |
| WO | WO-2014196841 A1 | 12/2014 |
| WO | WO-2014204281 A1 | 12/2014 |
| WO | WO-2015060673 A1 | 4/2015 |
| WO | WO-2015076621 A1 | 5/2015 |
| WO | WO-2015093854 A1 | 6/2015 |
| WO | WO-2015156649 A1 | 10/2015 |
| WO | WO-2015167067 A1 | 11/2015 |

OTHER PUBLICATIONS

International Search Report for International Application No. PCT/KR2014/005508, Korean Intellectual Property Office, Republic of Korea, dated Oct. 14, 2014, 8 pages.
Mattson, M.P., "Pathways Towards and Away From Alzheimer's Disease," Nature 430(7000):631-639, Nature Publishing Group, England (2004).
McConnell, J.D., et al., "The Effect of Finasteride on the Risk of Acute Urinary Retention and the Need for Surgical Treatment Among Men with Benign Prostatic Hyperplasia. Finasteride Long-term Efficacy and Safety Study Group," The New England Journal of Medicine 338(9):557-563, Massachusetts Medical Society, United States (1998).
NCBI, Reference Sequence: XP_003776612.1 (Jul. 17, 2012).
Perez, R.G., et al., "The Beta-amyloid Precursor Protein of Alzheimer's Disease Enhances Neuron Viability and Modulates Neuronal Polarity," The Journal of Neuroscience 17(24):9407-9414, Society for Neuroscience, United States (1997).
Rheumatoid Arthritis from Merck Manual, accessed on Apr. 21, 2016, pp. 1-18.
Schenk, D., et al., "Immunization with Amyloid-beta Attenuates Alzheimer-disease-like Pathology in the PDAPP Mouse," Nature 400(6740):173-177, Nature Publishing Group, England (1999).
Van Coppenolle, F., et al., "Effects of Hyperprolactinemia on Rat Prostate Growth: Evidence of Androgeno-dependence," American Journal of Physiology. Endocrinology and Metabolism 280(1):E120-E129, American Physiological Society, United States (2001).
Written Opinion for International Application No. PCT/KR2014/005508, Korean Intellectual Property Office, Republic of Korea, dated Oct. 14, 2014, 13 pages.
Altschul, S.F., et al., "Basic Local Alignment Search Tool," Journal of Molecular Biology 215(3):403-410, Elsevier, England (1990).
Bernhardt, S.L., et al., "Telomerase Peptide Vaccination of Patients with Non-Resectable Pancreatic Cancer: A Dose Escalating Phase I/II Study," British Journal of Cancer 95(11): 1474-1482, Nature Publishing Group on behalf of Cancer Research, England (2006).
Bonaldi, T., et al., "Monocytic Cells Hyperacetylate Chromatin Protein HMGB1 to Redirect it Towards Secretion," The EMBO Journal 22(20):5551-5560, Wiley Blackwell, England (2003).
Brandenburg, K., et al., "Peptide-based Treatment of Sepsis," Applied Microbiology and Biotechnology 90(3):799-808, Springer International, Germany (2011).
Brunsvig, P.F., et al., "Telomerase Peptide Vaccination in NSCLC: A Phase II Trial in Stage III Patients Vaccinated after Chemoradiotherapy and an 8-year Update on a Phase I/II Trial," Clinical Cancer Research 17(21):6847-6857, The Association, United States (2011).
Cho, Y.J., "GemVax & Kael (082270)," Hana Daetoo Securities, Company Report, Sep. 10, 2012, pp. 1-8.
Choi, S.G., "Recent Advances in Cancer Cachexia," Journal of Korean Oncology Nursing 11(1):20-25 (2011).
Co-pending U.S. Appl. No. 14/413,732, inventor Sang Jae Kim, filed Jul. 11, 2013 (Not Published).
Co-pending U.S. Appl. No. 14/896,358, inventor Sang Jae Kim, filed Dec. 4, 2015 (Not Published).
Co-pending U.S. Appl. No. 14/899,746, inventor Sang Jae Kim, filed Apr. 12, 2015 (Not Published).
Dahlgren, K.N., et al., "Oligomeric and Fibrillar Species of Amyloid-beta Peptides Differentially Affect Neuronal Viability," Journal of Biological Chemistry 277(35):32046-32053, American Society for Biochemistry and Molecular Biology, United States (2002).
Dinarello, C.A., "Interleukin-1 in the Pathogenesis and Treatment of Inflammatory Diseases," Blood 117(14):3720-3732, American Society of Hematology, United States (2011).
Engineer, D.R. and Garcia, J.M., "Leptin in Anorexia and Cachexia Syndrome," International Journal of Peptides 2012:Article ID 287457, Hindawi Publishing Corporation, United States (2012).
Fire, A., et al., "Potent and Specific Genetic Interference by Double-stranded RNA in Caenorhabditis Elegans," Nature 391(6669):806-811, Nature Publishing Group, England (1998).
Fittipaldi, A., et al., "Cell Membrane Lipid Rafts Mediate Caveolar Endocytosis of HIV-1 Tat Fusion Proteins," Journal of Biological Chemistry 278(36): 34141-34149, American Society for Biochemistry and Molecular Biology, United States(2003).
Fonseca, S.B., et al., "Recent Advances in the Use of Cell-Penetrating Peptides for Medical and Biological Applications," Advanced Drug Delivery Reviews 61(11):953-964, Elsevier Science Publishers, Netherlands (2009).
Fujii, H., et al., "Telomerase Insufficiency in Rheumatoid Arthritis," Proceedings of the National Academy of Sciences USA 106(11):4360-4365, National Academy of Sciences, United States (2009).
GemVax Receives Report on Anti-Inflammatory Mechanism, The Asia Economy Daily, Article written on May 7, 2013.
Ghaneh, P., et al., "Biology and Management of Pancreatic Cancer," Gut 56(8):1134-1152, British Medical Association, England (2007).
Granger, D.N. and Korthuis, R.J., "Physiologic Mechanisms of Postischemic Tissue Injury," Annual Review of Physiology 57:311-332, Annual Reviews, United States (1995).

(56) References Cited

OTHER PUBLICATIONS

Gunturu, K.S., et al., "Immunotherapy Updates in Pancreatic Cancer: Are we there yet?," Therapeutic Advances in Medical Oncology 5(1): 81-89, Sage, England (2013).
Heitz, F., et al., "Twenty Years of Cell-Penetrating Peptides: From Molecular Mechanisms to Therapeutics," British Journal of Pharmacology 157(2):195-206, Wiley, England (2009).
Hse, "Rheumatoid arthritis," http://www.hse.ie/portal/eng, accessed at http://www.hse.ie/portal/eng/health/az/R/Rheumatoid-arthritis/, 14 pages (2013) <http:></http:>.
International Preliminary Report on Patentability for International Application No. PCT/EP2013/059460, International Bureau of WIPO, Switzerland, dated Nov. 11, 2014, 5 pages.
International Preliminary Report on Patentability for International Application No. PCT/KR2013/004145, The International Bureau of WIPO, Switzerland, dated Nov. 11, 2014, 14 pages.
International Preliminary Report on Patentability for International Application No. PCT/KR2013/004176, The International Bureau of WIPO, Switzerland, dated Nov. 11, 2014, 14 pages.
International Preliminary Report on Patentability for International Application No. PCT/KR2013/006218, The International Bureau of WIPO, Switzerland, dated Jan. 13, 2015, 27 pages.
International Preliminary Report on Patentability for International Application No. PCT/KR2013/008438, The International Bureau of WIPO, Switzerland, dated Mar. 24, 2015, 6 pages.
International Preliminary Report on Patentability for International Application No. PCT/KR2013/008445, The International Bureau of WIPO, Switzerland, dated Mar. 24, 2015, 7 pages.
International Preliminary Report on Patentability for International Patent Application No. PCT/KR2013/004156, The International Bureau of WIPO, Geneva, Switzerland, dated Nov. 11, 2014, 15 pages.
International Search Report for International Application No. PCT/KR2014/003425, Korean Intellectual Property Office, Republic of Korea, dated Jul. 21, 2014, 8 pages.
International Search Report for International Application No. PCT/EP2013/059460, European Patent Office, Netherlands, dated Jul. 3, 2013, 5 pages.
International Search Report for International Application No. PCT/KR2013/004145, Korean Intellectual Property Office, Republic of Korea, dated Aug. 14, 2013, 10 pages.
International Search Report for International Application No. PCT/KR2013/004176, Korean Intellectual Property Office, Republic of Korea, dated Aug. 6, 2013, 10 pages.
International Search Report for International Application No. PCT/KR2013/006218, Korean Intellectual Property Office, Republic of Korea, dated Sep. 26, 2013, 8 pages.
International Search Report for International Application No. PCT/KR2013/008438, Korean Intellectual Property Office, Republic of Korea, dated Dec. 23, 2013, 3 pages.
International Search Report for International Application No. PCT/KR2013/008445, Korean Intellectual Property Office, Republic of Korea, dated Dec. 23, 2013, 4 pages.
International Search Report for International Patent Application No. PCT/KR2013/004156, Korean Intellectual Property Office, Republic of Korea, dated Aug. 14, 2013, 10 pages.
International Search Report for International Application No. PCT/KR2013/008459, Korean Intellectual Property Office, Republic of Korea, dated Dec. 23, 2013, 8 pages.
Kern, K.A. and Norton, J.A., "Cancer Cachexia," Journal of Parenteral and Enteral Nutrition 12(3):286-298, Sage Publications, United States (1988).
Kim, H.O. and Lee, S.I., "Experimental Animal Models for Rheumatoid Arthritis: Methods and Applications," Journal of Rheumatic Diseases 19(4):189-195 (2012).
Kyte, J.A., "Cancer Vaccination with Telomerase Peptide GV1001," Expert Opinion on Investigational Drugs 18(5):687-694, Taylor & Francis, England (2009).
Lahdevirta, J., et al., "Elevated Levels of Circulating Cachectin/tumor Necrosis Factor in Patients with Acquired Immunodeficiency Syndrome," American Journal of Medicine 85(3):289-291, Excerpta Medica, United States (1988).
Laviano, A., et al., "Therapy Insight: Cancer Anorexia-cachexia Syndrome—When All You Can Eat is Yourself," Nature Clinical Practice. Oncology 2(3):158-165, Nature Publishing Group, England (2005).
Lee, S.A., et al., "Heat Shock Protein-Mediated Cell Penetration and Cytosolic Delivery of Macromolecules by a Telomerase-Derived Peptide Vaccine," Biomaterials 34(30):7495-7505, Elsevier Science, Netherlands (2013).
Luft, R., et al., "A Case of Severe Hypermetabolism of Nonthyroid Origin with a Defect in the Maintenance of Mitochondrial Respiratory Control: A Correlated Clinical, Biochemical, and Morphological Study," Journal of Clinical Investigation 41:1776-1804, American Society for Clinical Investigation, United States (1962).
Martinez, P. and Blasco, M.A., "Telomeric and Extra-telomeric Roles for Telomerase and the Telomere-binding Proteins," Nature Reviews Cancer 11(3):161-176, Nature Publishing Group, England (2011).
Modica-Napolitano, J.S. and Singh, K.K., "Mitochondria as Targets for Detection and Treatment of Cancer," Expert Reviews in Molecular Medicine 4(9):1-19, Cambridge University Press, England (2002).
Myers, L.K., et al., "Collagen-Induced Arthritis, an Animal Model of Autoimmunity," Life Sciences 61(19):1861-1878, Elsevier, Netherlands (1997).
National Horizon Scanning Centre News on Emerging Technologies in Healthcare, GV1001 for Advanced and/or Metastatic Pancreatic Cancer, Published Apr. 2008.
Novina, C.D. and Sharp, P.A., "The RNAi Revolution," Nature 430(6996):161-164, Nature Publishing Group, England (2004).
Oh, H., et al., "Telomerase Reverse Transcriptase Promotes Cardiac Muscle Cell Proliferation, Hypertrophy, and Survival," Proceedings of the National Academy of Sciences 98(18): 10308-10313, National Academy of Sciences, United States (2001).
Pearson, W.R. and Lipman, D.J., "Improved Tools for Biological Sequence Comparison,"Proceedings of the National Academy of Sciences USA 85(8):2444-2448, National Academy of Sciences, United States (1988).
Rana, T.M., "Illuminating the Silence: Understanding the Structure and Function of Small RNAs," Nature Reviews. Molecular Cell Biology 8(1):23-36, Nature Publishing Group, England (2007).
Roubenoff, R., et al., "Adjuvant Arthritis as a Model of Inflammatory Cachexia," Arthritis and Rheumatism 40(3):534-539, Wiley-Blackwell, United States (1997).
Smith, D.B. and Johnson, K.S., "Single-step Purification of Polypeptides Expressed in *Escherichia coli* as Fusions with Glutathione S-transferase," Gene 67(1):31-40, Elsevier, Netherlands (1988).
Smith, T.F. and Waterman, M.S., "Comparison of Biosequences," Advances in Applied Mathematics 2(4):482-489, Academic Press, Inc., United States (1981).
Southern Cross, "Rheumatoid arthritis—causes, symptoms, and treatment," https://www.southerncross.co.nz/, accessed at https://www.southerncross.co.nz/AboutTheGroup/HealthResources/MedicalLibrary/tabid/178/vw/1/itemID/124/Rheumatoid-arthritis-causes-symptoms-treatment.aspx, last reviewed on May 31, 2013, 5 pages<https;></https:>.
Stevenson, C.L., "Advances in Peptide Pharmaceuticals," Current Pharmaceutical Biotechnology 10(1):122-137, Bentham Science Publishers, Netherlands (2009).
Taylor, P.C. and Feldmann, M., "Anti-TNF Biologic Agents: Still the Therapy of Choice for Rheumatoid Arthritis," Nature Reviews. Rheumatology 5(10):578-582, Macmillan Publishers Limited, England (2009).
Thompson, J.D., et al., "Clustal W: Improving the Sensitivity of Progressive Multiple Sequence Alignment Through Sequence Weighting, Position-specific Gap Penalties and Weight Matrix Choice," Nucleic Acids Research 22(22):4673-4680, Oxford University Press, England (1994).
Tisdale, M.J., "Mechanisms of Cancer Cachexia," Physiological Reviews 89(2):381-410, American Physiological Society, United States (2009).

(56) References Cited

OTHER PUBLICATIONS

Tomari Y. and Zamore, P.D., "Perspective: Machines for RNAi," Genes and Development 19(5):517-529, Cold Spring Harbor Laboratory Press, United States (2005).
Walsmith, J. and Roubenoff, R., "Cachexia in Rheumatoid Arthritis," International Journal of Cardiology 85(1):89-99, Elsevier, Netherlands (2002).
Written Opinion for International Application No. PCT/EP2013/059460, European Patent Office, Germany, dated Jul. 3, 2013, 4 pages.
Written Opinion for International Application No. PCT/KR2013/004145, Korean Intellectual Property Office, Republic of Korea, dated Aug. 14, 2013, 13 pages.
Written Opinion for International Application No. PCT/KR2013/004176, Korean Intellectual Property Office, Republic of Korea, dated Aug. 6, 2013, 7 pages.
Written Opinion for International Application No. PCT/KR2013/006218, Korean Intellectual Property Office, Republic of Korea, dated Sep. 26, 2013, 26 pages.
Written Opinion for International Application No. PCT/KR2013/008438, Korean Intellectual Property Office, Republic of Korea, dated Dec. 23, 2013, 5 pages.
Written Opinion for International Application No. PCT/KR2013/008445, Korean Intellectual Property Office, Republic of Korea, dated Dec. 23, 2013, 6 pages.
Written Opinion for International Application No. PCT/KR2013/008459, Korean Intellectual Property Office, Republic of Korea, dated Dec. 23, 2013, 9 pages.
Written Opinion for International Patent Application No. PCT/KR2013/004156, Korean Intellectual Property Office, Republic of Korea, dated Aug. 14, 2013, 13 pages.
Written Opinion for International Application No. PCT/KR2014/003425, Korean Intellectual Property Office, Republic of Korea, dated Jul. 21, 2014, 13 pages.
Yankner, B.A., et al., "Neurotrophic and Neurotoxic Effects of Amyloid Beta Protein: Reversal by Tachykinin Neuropeptides," Science 250(4978):279-282, American Association for the Advancement of Science, United States (1990).
Inderberg-Suso, E.M., et al., "Widespread CD4+ T-cell Reactivity to Novel hTERT Epitopes following Vaccination of Cancer Patients with a Single hTERT Peptide GV1001," Oncoimmunology 1(5):670-686, Taylor & Francis, United States (2012).
International Preliminary Report on Patentability for International Application No. PCT/KR2014/005031, The International Bureau of WIPO, Switzerland, dated Dec. 8, 2015, 8 pages.
International Search Report for International Application No. PCT/KR2014/005031, Korean Intellectual Property Office, Republic of Korea, dated Sep. 22, 2014, 6 pages.
Kokhaei, P., et al., "Telomerase (hTERT 611-626) Serves as a Tumor Antigen in B-cell Chronic Lymphocytic Leukemia and Generates Spontaneously Antileukemic, Cytotoxic T Cells," Experimental Hematology 35(2):297-304, Elsevier Science Inc., Netherlands (2007).
Schlapbach, C., et al., "Telomerase-specific GV1001 Peptide Vaccination Fails to Induce Objective Tumor Response in Patients with Cutaneous T Cell Lymphoma," Journal of Dermatological Science 62(2):75-83, Elsevier, Netherlands (2011).
Vennela, B., et al., "Current and Future Strategies for Therapy of Pancreatic Cancer," International Journal of Research in Pharmacy and Medicine 2(3):728-740 (2012).
Written Opinion for International Application No. PCT/KR2014/005031, Korean Intellectual Property Office, Republic of Korea, dated Sep. 22, 2014, 7 pages.
International Search Report for International Application No. PCT/KR2014/010035, Korean Intellectual Property Office, Republic of Korea, dated Feb. 2, 2015, 8 pages.
Shay, J.W., et al., "Telomerase therapeutics for cancer: challenges and new directions," Nature Reviews Drug Discovery 5(7): 577-584, Nature Publishing Group, England (2006).

Beer, T.M., et al., "Phase II Study of Weekly Docetaxel in Symptomatic Androgen-independent Prostate Cancer," Annals of Oncology 12(9):1273-1279, Oxford University Press, England (2001).
Bohonowych, J.E., et al., "Comparative Analysis of Novel and Conventional HSP90 Inhibitors on HIF Activity and Angiogenic Potential in Clear Cell Renal Cell Carcinoma: Implications for Clinical Evaluation," BMC Cancer 11:520, BioMed Central, England (2011).
Bruns, A.F., et al., "A Heat-shock Protein Axis Regulates VEGFR2 Proteolysis, Blood Vessel Development and Repair," PloS One 7(11):e48539, Public Library of Science, United States (2012).
Calderwood, S.K., et al., "Heat Shock Proteins in Cancer: Chaperones of Tumorigenesis," Trends in Biochemical Sciences 31(3):164-172, Elsevier Trends Journals, England (2006).
Dempsey, N.C., et al., "Differential Heat Shock Protein Localization in Chronic Lymphocytic Leukemia," Journal of Leukocyte Biology 87(3):467-476, Society for Leukocyte Biology, United States (2010).
Du, R., et al., "HIF1alpha Induces the Recruitment of Bone Marrow-derived Vascular Modulatory Cells to Regulate Tumor Angiogenesis and Invasion," Cancer Cell 13(3):206-220, Cell Press, United States (2008).
Eustace, B.K. and Jay, D.G., "Extracellular Roles for the Molecular Chaperone, Hsp90," Cell Cycle 3(9):1098-1100, Taylor & Francis, United States (2004).
Eustace, B.K. and Jay, D.G., "Functional Proteomic Screens Reveal an Essential Extracellular Role for Hsp90 Alpha in Cancer Cell Invasiveness," Nature Cell Biology 6(6):507-514, Macmillan Magazines Ltd., England (2004).
Evans, C.G., et al., "Heat Shock Protein 70 (Hsp70) as an Emerging Drug Target," Journal of Medicinal Chemistry 53(12):4585-4602, American Chemical Society, United States (2010).
Ferrarini, M., et al., "Unusual Expression and Localization of Heat-shock Proteins in Human Tumor Cells," International Journal of Cancer51(4):613-619, Wiley-Liss, United States (1992).
Garcia-Carbonero, R., et al., "Inhibition of HSP90 Molecular Chaperones: Moving Into the Clinic," The Lancet Oncology 14(9):e358-e369, Lancet Publishing Group, England (2013).
Henry, J.Y., et al., "Lenalidomide Enhances the Anti-prostate Cancer Activity of Docetaxel in vitro and in vivo," The Prostate 72(8):856-867, Wiley-Liss, United States (2012).
International Preliminary Report on Patentability for International Application No. PCT/KR2014/011280, The International Bureau of WIPO, Geneva, Switzerland, dated May 24, 2016, 15 pages.
International Search Report for International Application No. PCT/KR2014/011280, Korean Intellectual Property Office, Republic of Korea, dated Feb. 11, 2015, 12 pages.
International Search Report for International Application No. PCT/KR2014/012502, Korean Intellectual Property Office, Republic of Korea, dated Mar. 11, 2015, 10 pages.
International Preliminary Report on Patentability for International Application No. PCT/KR2014/012502, The International Bureau of WIPO, Geneva, Switzerland, dated Jun. 21, 2016, 22 pages.
Jaattela, M., "Over-expression of Hsp70 Confers Tumorigenicity to Mouse Fibrosarcoma Cells," International Journal of Cancer 60(5):689-693, Wiley-Liss, United States (1995).
Jemal, A., et al., "Cancer Statistics, 2008," CA: A Cancer Journal for Clinicians 58(2):71-96, Wiley, United States (2008).
Kim, B.K., et al., "Tumor-suppressive Effect of a Telomerase-derived Peptide by Inhibiting Hypoxia-induced HIF-1α-VEGF Signaling Axis," Biomaterials 35(9):2924-2933, Elsevier Science, Netherlands (2014).
Kocsis, J., et al., "Serum Level of Soluble 70-kD Heat Shock Protein is Associated With High Mortality in Patients With Colorectal Cancer Without Distant Metastasis," Cell Stress & Chaperones 15(2):143-151, Springer, Netherlands (2010).
Liu, Q.J., et al., "Rapamycin Enhances the Susceptibility of Both Androgen-dependent and—independent Prostate Carcinoma Cells to Docetaxel," Chinese Medical Journal 123(3):356-360, Chinese Medical Association, China (2010).
Morano, K.A., "New Tricks for an Old Dog: the Evolving World of Hsp70," Annals of the New York Academy of Sciences 1113:1-14, Blackwell, United States (2007).

(56) References Cited

OTHER PUBLICATIONS

Murphy, M.E., "The Hsp70 Family and Cancer," Carcinogenesis 34(6):1181-1188, Irl Press, England (2013).
Nagaraju, G.P., et al., "Antiangiogenic Effects of Ganetespib in Colorectal Cancer Mediated Through Inhibition of HIF-1α and STAT-3," Angiogenesis 16(4):903-917, Springer, Germany (2013).
Pfosser, A., et al., "Liposomal HSP90 Cdna Induces Neovascularization via Nitric Oxide in Chronic Ischemia," Cardiovascular Research 65(3):728-736, Oxford Journals, England (2005).
Powers, M.V., et al., "Targeting HSP70: the Second Potentially Druggable Heat Shock Protein and Molecular Chaperone?," Cell Cycle 9(8):1542-1550, Taylor & Francis, United States (2010).
Sayers, S., et al., "Vaxjo: A Web-based Vaccine Adjuvant Database and its Application for Analysis of Vaccine Adjuvants and their Uses in Vaccine Development," Journal of Biomedicine and Biotechnology 2012:1-13, Article ID 831486, Hindawi Publishing Corporation, United States (2012).
Seo, J.S., et al., "T Cell Lymphoma in Transgenic Mice Expressing the Human Hsp70 Gene," Biochemical and Biophysical Research Communications 218(2):582-587, Elsevier, United States (1996).
Sun, J., et al., "Induction of Angiogenesis by Heat Shock Protein 90 Mediated by Protein Kinase Akt and Endothelial Nitric Oxide Synthase," Arteriosclerosis, Thrombosis, and Vascular biology 24(12):2238-2244, Lippincott Williams & Wilkins, United States (2004).
Uehara, Y., "Natural Product Origins of Hsp90 Inhibitors," Current Cancer Drug Targets 3(5):325-330, Bentham Science Publishers, Netherlands (2003).
Vanbuskirk, A., et al., "A Peptide Binding Protein Having a Role in Antigen Presentation is a Member of the HSP70 Heat Shock Family," The Journal of Experimental Medicine 170(6):1799-1809, Rockefeller University Press, United States (1989).
Volloch, V.Z. and Sherman, M.Y., "Oncogenic Potential of Hsp72," Oncogene 18(24):3648-3651, Nature Publishing Group, England (1999).
Written Opinion for International Application No. PCT/KR2014/011280, Korean Intellectual Property Office, Republic of Korea, dated Feb. 11, 2015, 14 pages.
Written Opinion for International Application No. PCT/KR2014/012502, Korean Intellectual Property Office, Republic of Korea, dated Mar. 11, 2015, 20 pages.
Yeh, C.H., et al., "Clinical Correlation of Circulating Heat Shock Protein 70 in Acute Leukemia," Leukemia Research 34(5):605-609, Pergamon Press, England (2010).
Zhou, J., et al., "PI3K/Akt is Required for Heat Shock Proteins to Protect Hypoxia-inducible Factor 1alpha From pVHL-independent Degradation," The Journal of Biological Chemistry 279(14):13596-13513, American Society for Biochemistry and Molecular Biology, United States (2004).
Heldin, C.H., et al., "TGF-Beta Signalling from Cell Membrane to Nucleus through SMAD Proteins," Nature 390(6659):465-471, Nature Publishing Group, England (1997).
International Preliminary Report on Patentability for Application No. PCT/KR2014/004752, The International Bureau of WIPO, Switzerland, dated Nov. 1, 2016, 23 pages.
International Preliminary Report on Patentability for Application No. PCT/KR2015/003642, The International Bureau of WIPO, Switzerland, dated Oct. 12, 2016, 18 pages.
International Search Report for International Application No. PCT/KR2014/004752, Korean Intellectual Property Office, Republic of Korea, dated Jan. 16, 2015, 10 pages.
International Search Report for International Application No. PCT/KR2015/003642, Korean Intellectual Property Office, Republic of Korea, dated Jul. 3, 2015, 8 pages.
Massague, J., "Tgf-Beta Signal Transduction," Annual Review of Biochemistry 67:753-791, Annual Reviews, United States (1998).
Song, J., et al., "Characterization and Fate of Telomerase-Expressing Epithelia during Kidney Repair," Journal of the American Society of Nephrology 22(12):2256-2265, American Society of Nephrology, United States (2011).
Wang, W., et al., "Alleviating the Ischemia-Reperfusion Injury of Donor Liver by Transfection of Exogenous hTERT Genes," Transplantation Proceedings 41(5):1499-1503, Elsevier Science, United States (2009).
Written Opinion for International Application No. PCT/KR2014/004752, Korean Intellectual Property Office, Republic of Korea, dated Jan. 16, 2015, 21 pages.
Written Opinion for International Application No. PCT/KR2015/003642, Korean Intellectual Property Office, Republic of Korea, dated Jul. 3, 2015, 16 pages.
Yi, A., et al., "Radiation-Induced Complications after Breast Cancer Radiation Therapy: a Pictorial Review of Multimodality Imaging Findings," Korean Journal of Radiology 10(5):496-507, Korean Society of Radiology, Korea (2009).
Zhang, H., et al., "Inhibiting TGFβ1 has a Protective Effect on Mouse Bone Marrow Suppression Following Ionizing Radiation Exposure in Vitro," Journal of Radiation Research 54(4):630-636, Oxford University Press, England (2013).
Co-pending U.S. Appl. No. 15/105,289, inventors Kim, Sang Jae, filed Jun. 16, 2016 (Not Yet Published).
Co-pending U.S. Appl. No. 15/303,370, inventors Kim, Sang Jae, filed Oct. 11, 2016 (Not Yet Published).
Co-pending U.S. Appl. No. 15/307,632, inventors Kim, Sang Jae, filed Oct. 28, 2016 (Not Yet Published).
Co-pending U.S. Appl. No. 15/346,870, inventors Kim, Sang Jae, filed Nov. 9, 2016 (Not Yet Published).
International Preliminary Report on Patentability for International Application No. PCT/KR2014/010035, Korean Intellectual Property Office, Republic of Korea, dated Apr. 26, 2016, 13 pages.
Written Opinion for International Application No. PCT/KR2014/010035, Korean Intellectual Property Office, Republic of Korea, dated Feb. 2, 2015, 11 pages.

* cited by examiner

US 9,907,838 B2

SEQUENCE LISTING

<160> NUMBER OF SEQ ID NOS: 2

<210> SEQ ID NO 1
<211> LENGTH: 16
<212> TYPE: PRT
<213> ORGANISM: Homo sapiens

<400> SEQUENCE: 1

```
Glu Ala Arg Pro Ala Leu Leu Thr Ser Arg Leu Arg Phe Ile Pro Lys
 1               5                  10                  15

<210> SEQ ID NO 2
<211> LENGTH: 1132
<212> TYPE: PRT
<213> ORGANISM: Homo sapiens

<400> SEQUENCE: 2

Met Pro Arg Ala Pro Arg Cys Arg Ala Val Arg Ser Leu Leu Arg Ser
 1               5                  10                  15

His Tyr Arg Glu Val Leu Pro Leu Ala Thr Phe Val Arg Arg Leu Gly
                20                  25                  30

Pro Gln Gly Trp Arg Leu Val Gln Arg Gly Asp Pro Ala Ala Phe Arg
            35                  40                  45

Ala Leu Val Ala Gln Cys Leu Val Cys Val Pro Trp Asp Ala Arg Pro
        50                  55                  60

Pro Pro Ala Ala Pro Ser Phe Arg Gln Val Ser Cys Leu Lys Glu Leu
65                  70                  75                  80

Val Ala Arg Val Leu Gln Arg Leu Cys Glu Arg Gly Ala Lys Asn Val
                85                  90                  95

Leu Ala Phe Gly Phe Ala Leu Leu Asp Gly Ala Arg Gly Gly Pro Pro
                100                 105                 110

Glu Ala Phe Thr Thr Ser Val Arg Ser Tyr Leu Pro Asn Thr Val Thr
            115                 120                 125

Asp Ala Leu Arg Gly Ser Gly Ala Trp Gly Leu Leu Leu Arg Arg Val
        130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro Pro His Ala Ser Gly
                180                 185                 190

Pro Arg Arg Arg Leu Gly Cys Glu Arg Ala Trp Asn His Ser Val Arg
            195                 200                 205

Glu Ala Gly Val Pro Leu Gly Leu Pro Ala Pro Gly Ala Arg Arg Arg
        210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255

Ala His Pro Gly Arg Thr Arg Gly Pro Ser Asp Arg Gly Phe Cys Val
                260                 265                 270

Val Ser Pro Ala Arg Pro Ala Glu Ala Thr Ser Leu Glu Gly Ala
            275                 280                 285

Leu Ser Gly Thr Arg His Ser His Pro Ser Val Gly Arg Gln His His
        290                 295                 300

Ala Gly Pro Pro Ser Thr Ser Arg Pro Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

Asp Lys Glu Gln Leu Arg Pro Ser Phe Leu Leu Ser Ser Leu Arg Pro
                340                 345                 350

Ser Leu Thr Gly Ala Arg Arg Leu Val Glu Thr Ile Phe Leu Gly Ser
            355                 360                 365
```

```
Arg Pro Trp Met Pro Gly Thr Pro Arg Arg Leu Pro Arg Leu Pro Gln
    370                 375                 380
Arg Tyr Trp Gln Met Arg Pro Leu Phe Leu Glu Leu Leu Gly Asn His
385                 390                 395                 400
Ala Gln Cys Pro Tyr Gly Val Leu Leu Lys Thr His Cys Pro Leu Arg
                405                 410                 415
Ala Ala Val Thr Pro Ala Ala Gly Val Cys Ala Arg Glu Lys Pro Gln
            420                 425                 430
Gly Ser Val Ala Ala Pro Glu Glu Asp Thr Asp Pro Arg Arg Leu
        435                 440                 445
Val Gln Leu Leu Arg Gln His Ser Ser Pro Trp Gln Val Tyr Gly Phe
    450                 455                 460
Val Arg Ala Cys Leu Arg Arg Leu Val Pro Pro Gly Leu Trp Gly Ser
465                 470                 475                 480
Arg His Asn Glu Arg Arg Phe Leu Arg Asn Thr Lys Lys Phe Ile Ser
                485                 490                 495
Leu Gly Lys His Ala Lys Leu Ser Leu Gln Glu Leu Thr Trp Lys Met
            500                 505                 510
Ser Val Arg Asp Cys Ala Trp Leu Arg Arg Ser Pro Gly Val Gly Cys
    515                 520                 525
Val Pro Ala Ala Glu His Arg Leu Arg Glu Glu Ile Leu Ala Lys Phe
530                 535                 540
Leu His Trp Leu Met Ser Val Tyr Val Val Glu Leu Leu Arg Ser Phe
545                 550                 555                 560
Phe Tyr Val Thr Glu Thr Thr Phe Gln Lys Asn Arg Leu Phe Phe Tyr
                565                 570                 575
Arg Lys Ser Val Trp Ser Lys Leu Gln Ser Ile Gly Ile Arg Gln His
            580                 585                 590
Leu Lys Arg Val Gln Leu Arg Glu Leu Ser Glu Ala Glu Val Arg Gln
        595                 600                 605
His Arg Glu Ala Arg Pro Ala Leu Leu Thr Ser Arg Leu Arg Phe Ile
    610                 615                 620
Pro Lys Pro Asp Gly Leu Arg Pro Ile Val Asn Met Asp Tyr Val Val
625                 630                 635                 640
Gly Ala Arg Thr Phe Arg Arg Glu Lys Arg Ala Glu Arg Leu Thr Ser
                645                 650                 655
Arg Val Lys Ala Leu Phe Ser Val Leu Asn Tyr Glu Arg Ala Arg Arg
            660                 665                 670
Pro Gly Leu Leu Gly Ala Ser Val Leu Gly Leu Asp Asp Ile His Arg
        675                 680                 685
Ala Trp Arg Thr Phe Val Leu Arg Val Arg Ala Gln Asp Pro Pro Pro
    690                 695                 700
Glu Leu Tyr Phe Val Lys Val Asp Val Thr Gly Ala Tyr Asp Thr Ile
705                 710                 715                 720
Pro Gln Asp Arg Leu Thr Glu Val Ile Ala Ser Ile Ile Lys Pro Gln
                725                 730                 735
Asn Thr Tyr Cys Val Arg Arg Tyr Ala Val Val Gln Lys Ala Ala His
            740                 745                 750
Gly His Val Arg Lys Ala Phe Lys Ser His Val Ser Thr Leu Thr Asp
        755                 760                 765
Leu Gln Pro Tyr Met Arg Gln Phe Val Ala His Leu Gln Glu Thr Ser
    770                 775                 780
```

```
                                            -continued
Pro Leu Arg Asp Ala Val Val Ile Glu Gln Ser Ser Leu Asn Glu
785                 790                 795                 800

Ala Ser Ser Gly Leu Phe Asp Val Phe Leu Arg Phe Met Cys His His
                805                 810                 815

Ala Val Arg Ile Arg Gly Lys Ser Tyr Val Gln Cys Gln Gly Ile Pro
                820                 825                 830

Gln Gly Ser Ile Leu Ser Thr Leu Leu Cys Ser Leu Cys Tyr Gly Asp
            835                 840                 845

Met Glu Asn Lys Leu Phe Ala Gly Ile Arg Arg Asp Gly Leu Leu Leu
        850                 855                 860

Arg Leu Val Asp Asp Phe Leu Leu Val Thr Pro His Leu Thr His Ala
865                 870                 875                 880

Lys Thr Phe Leu Arg Thr Leu Val Arg Gly Val Pro Glu Tyr Gly Cys
                885                 890                 895

Val Val Asn Leu Arg Lys Thr Val Val Asn Phe Pro Val Glu Asp Glu
                900                 905                 910

Ala Leu Gly Gly Thr Ala Phe Val Gln Met Pro Ala His Gly Leu Phe
            915                 920                 925

Pro Trp Cys Gly Leu Leu Leu Asp Thr Arg Thr Leu Glu Val Gln Ser
930                 935                 940

Asp Tyr Ser Ser Tyr Ala Arg Thr Ser Ile Arg Ala Ser Leu Thr Phe
945                 950                 955                 960

Asn Arg Gly Phe Lys Ala Gly Arg Asn Met Arg Arg Lys Leu Phe Gly
                965                 970                 975

Val Leu Arg Leu Lys Cys His Ser Leu Phe Leu Asp Leu Gln Val Asn
                980                 985                 990

Ser Leu Gln Thr Val Cys Thr Asn Ile Tyr Lys Ile Leu Leu Leu Gln
            995                 1000                1005

Ala Tyr Arg Phe His Ala Cys Val Leu Gln Leu Pro Phe His Gln Gln
    1010                1015                1020

Val Trp Lys Asn Pro Thr Phe Phe Leu Arg Val Ile Ser Asp Thr Ala
1025                1030                1035                1040

Ser Leu Cys Tyr Ser Ile Leu Lys Ala Lys Asn Ala Gly Met Ser Leu
                1045                1050                1055

Gly Ala Lys Gly Ala Ala Gly Pro Leu Pro Ser Glu Ala Val Gln Trp
            1060                1065                1070

Leu Cys His Gln Ala Phe Leu Leu Lys Leu Thr Arg His Arg Val Thr
        1075                1080                1085

Tyr Val Pro Leu Leu Gly Ser Leu Arg Thr Ala Gln Thr Gln Leu Ser
    1090                1095                1100

Arg Lys Leu Pro Gly Thr Thr Leu Thr Ala Leu Glu Ala Ala Ala Asn
1105                1110                1115                1120

Pro Ala Leu Pro Ser Asp Phe Lys Thr Ile Leu Asp
                1125                1130
```

COMPOSITION AND METHODS FOR TREATING ISCHEMIC DAMAGE

REFERENCE TO SEQUENCE LISTING SUBMITTED ELECTRONICALLY VIA EFS-WEB

The content of the electronically submitted sequence listing (Name: 2473_0840002_SeqListing_ST25.txt; 9,356 bytes; and Date of Creation: Oct. 15, 2015) was originally submitted in the International Application No. PCT/KR2014/003425 and is incorporated herein by reference in its entirety.

TECHNICAL FIELD

The present disclosure relates to a composition for treating and preventing an ischemic injury. More particularly, it relates to a composition containing a peptide derived from a telomerase, which is effective in treating and preventing an ischemic injury.

BACKGROUND ART

An ischemic injury refers to a tissue injury caused by restriction in blood supply to organs requiring blood supply such as the heart, brain, kidneys, etc. (myocardial infarction, cerebral infarction, renal infarction, etc.), leading to dysfunction of the organs and increased mortality rate. The ischemic injury causes fatal complications of the heart, brain, kidneys, etc., increases the risk of acute rejection in organ transplantation and, in the long term, decreases the survival rate of the transplanted organ.

Substantial shortage of oxygen supply due to ischemia induces a pathological condition known as hypoxia. Prolonged ischemia and hypoxia can lead to functional loss of tissue and even cell death. Various spontaneous and iatrogenic pathological conditions induce ischemia and hypoxia. Non-limiting examples include vascular obstructive disease, coronary thrombosis, cerebrovascular thrombosis, aneurysm rupture, systemic hemorrhage, crush injury, sepsis, severe skin burn, vascular ligation surgery (e.g., spinal ischemia following thoracoabdominal aneurysm surgery), cardiopulmonary bypass, organ transplantation, cardiopulmonary collapse (sudden cardiac death), suffocation, etc.

In general, ischemia and hypoxia caused thereby are treated by restoring blood and oxygen supply to a normal level by increasing systemic oxygen supply or removing the cause of vascular occlusion. When compared with the situation where ischemia or hypoxia is prolonged, it is expected an improved result may be obtained by restoring blood supply. However, during the restoration of blood and oxygen supply, cell death or functional loss may be additionally induced apart from the damage caused by ischemia or hypoxia.

The additional damage induced during the restoration of blood and oxygen supply is known as reperfusion injury. The paradoxical tissue injury caused by reperfusion injury appears to be similar to an acute inflammatory condition resulting from the adherence of inflammatory cells to the reperfused tissues, activation of the inflammatory cells and subsequent generation of free radicals [Granger et al. *Ann. Rev. Physiol.*, 57, 311-332, (1995)]. The generation of free radicals and other cytotoxic biomolecules within the reperfused tissue can induce cell death by activation of necrotic or apoptotic pathway.

Ischemic-reperfusion (IR) tissue injury occurring during organ transplantation results in deferred restoration of organ function after the organ transplantation and this often is an undesired prognostic sign in the maintenance of the function of the transplanted organ in the long term due to inflammatory tissue response. The initial ischemic-reperfusion injury occurring incidentally with the transplantation of organs, particularly kidneys, can lead to subsequent organ failure and transplant rejection.

Recently, renal ischemic-reperfusion injury (IRI) has been newly identified as one of acute inflammatory responses in which the inflammatory cells of both the innate immune system and the acquired immune system are involved.

A flap refers to a skin or tissue which is lifted from a site of the body and moved to another site, which includes a blood vessel that allows survival of the tissue. Flap surgery is used for lost soft tissue, chronic wound, etc. that cannot be treated with, for example, skin grafting. It is a surgical method the most frequently used in plastic and reconstructive surgery. In particular, it is advantageous in that primary reconstruction is possible through transplantation of various complex tissues including bone, tendon, muscle, nerve, etc., thereby allowing fast restoration. In the flap surgery, the survival rate of the flap is very important in the treatment of ischemic-reperfusion injury. Accordingly, a method of stably improving the flap survival rate will be very useful.

As described, an effective method for treating the frequently occurring ischemic-reperfusion injury is not readily available. Therefore, an effective method for preventing and treating ischemic-reperfusion injury will be valuable.

DISCLOSURE

Technical Problem

The inventors of the present disclosure have made efforts to develop a composition effective in treating and preventing ischemic-reperfusion injury and have completed the present disclosure.

The inventors of the present disclosure have found out that a peptide derived from a telomerase may have excellent effect of treating and preventing ischemic-reperfusion injury.

The present disclosure is directed to providing a composition effective in treating and preventing ischemic-reperfusion injury.

Technical Solution

In an aspect, the present disclosure provides a composition for treating and preventing an ischemic injury, containing a peptide comprising an amino acid sequence of SEQ ID NO 1, a peptide having 80% or more sequence identity with the amino acid sequence or a peptide which is a fragment thereof.

In an exemplary embodiment of the present disclosure, the fragment may comprise three or more amino acids.

In an exemplary embodiment of the present disclosure, the ischemic injury may be caused by one or more selected from a group consisting of ischemic-reperfusion injury, vascular disease, coronary thrombosis, cerebrovascular thrombosis, aneurysm rupture, systemic hemorrhage, crush injury, sepsis, skin burn, vascular ligation surgery, cardiopulmonary bypass, organ transplantation, cardiopulmonary collapse (sudden cardiac death) and suffocation.

In an exemplary embodiment of the present disclosure, the ischemic injury may be caused by ischemic-reperfusion injury.

In an exemplary embodiment of the present disclosure, the ischemic-reperfusion injury may be selected from a group consisting of cerebrovascular ischemic-reperfusion injury, renal ischemic-reperfusion injury, hepatic ischemic-reperfusion injury, ischemic-reperfusion cardiomyopathy, ischemic-reperfusion skin injury, gastrointestinal ischemic-reperfusion injury, intestinal ischemic-reperfusion injury, gastric ischemic-reperfusion injury, ischemic-reperfusion lung injury, pancreatic ischemic-reperfusion injury, ischemic-reperfusion skeletal muscle injury, ischemic-reperfusion abdominal muscle injury, ischemic-reperfusion limb injury, ischemic-reperfusion colitis, mesenteric ischemic-reperfusion injury and asymptomatic ischemic-reperfusion injury.

In an exemplary embodiment of the present disclosure, the ischemic-reperfusion injury may be caused by organ transplantation.

In an exemplary embodiment of the present disclosure, the ischemic-reperfusion injury may occur in the kidneys.

In an exemplary embodiment of the present disclosure, the ischemic-reperfusion injury may occur in a flap.

In an exemplary embodiment of the present disclosure, the peptide may be derived from human telomerase.

In an exemplary embodiment of the present disclosure, the composition may be a pharmaceutical composition.

In an exemplary embodiment of the present disclosure, the composition may be a food composition.

In another aspect, the present disclosure provides a method for treating and preventing an ischemic injury, including administering the above-described composition to a subject in need thereof.

Advantageous Effects

A peptide comprising an amino acid sequence of SEQ ID NO 1, a peptide having 80% or more sequence identity with the amino acid sequence or a peptide which is a fragment thereof has a superior effect of treating and preventing an ischemic injury. Accordingly, a composition containing the peptide may be effectively used for an ischemic injury, particularly for ischemic-reperfusion injury caused by organ transplantation, etc.

BEST MODE

Figure 1:
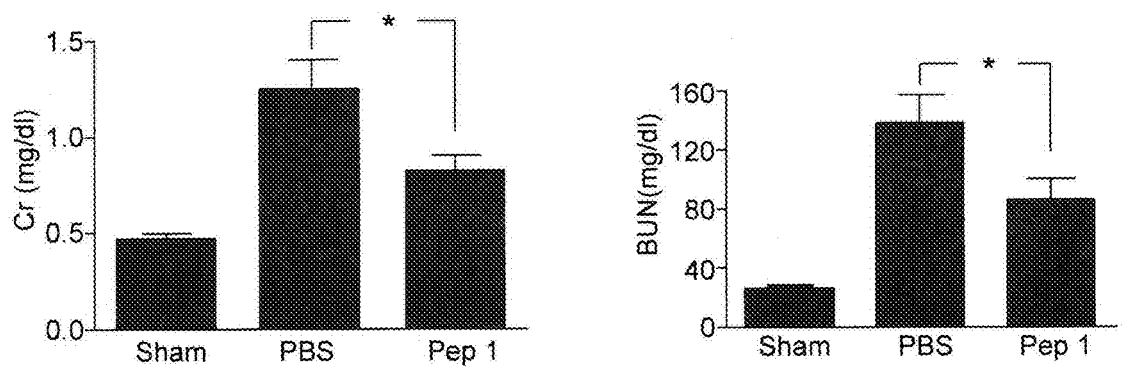
FIG. 1 shows a result of measuring blood urea nitrogen (BUN) and creatine levels 24 hours after ischemic reperfusion.

The present disclosure can be modified and embodied in various ways. Hereinafter, the present disclosure will be described in more detail through exemplary embodiments. However, the following examples are not intended to be limitative of the present disclosure. Rather, the present disclosure can be variously changed based on the appended claims. It is to be understood that the present disclosure includes any change, equivalent or substitute that falls within the technical idea and scope of the present disclosure. In the description, details of well-known features and techniques may be omitted to avoid unnecessarily obscuring the presented embodiments.

Telomere is known as a repetitive sequence of genetic material found at the ends of chromosomes that prevent chromosomes from damage or merging onto other chromosomes. The length of the telomere is shortened at each cell division, and after a certain number of cell division, the telomere length is extremely shortened to the extent in which the cell stops dividing and dies. On the other hand, the elongation of telomeres is known to extend the life span of a cell. For an example, cancer cells excrete an enzyme called telomerase, which prevents shortening of telomeres, thus resulting in proliferation of cancer cells. The inventors of the present disclosure have identified that a peptide derived from telomerase is effective in treating and preventing ischemic-reperfusion injury and have completed the present disclosure.

In an exemplary embodiment of the present disclosure, a peptide of SEQ ID NO: 1, a peptide which is a fragment of the peptide of SEQ ID NO: 1 or a peptide having 80% or more sequence identity with the peptides includes a peptide derived from telomerase, specifically human (*Homo sapiens*) telomerase.

The peptides disclosed herein may include peptides comprising an amino acid sequence at least 80%, at least 85%, at least 90%, at least 95%, at least 96%, at least 97%, at least 98%, at least 99% of sequence homology with the peptide of SEQ ID NO: 1 or a fragment thereof. Moreover, the peptides disclosed in the present invention may include peptides having differences from SEQ ID NO: 1 or a fragment thereof in at least one amino acids, at least 2 amino acids, at least 3 amino acids, at least 4 amino acids, at least 5 transformed amino acids, at least 6 transformed amino acids, or at least 7 amino acids.

In one embodiment of the present invention, changes in amino acids include modifications of peptide's physical and chemical characteristics. For example, amino acid modification can be performed for improving thermal stability of the peptide, altering substrate specificity, and changing the optimal pH.

The term "amino acid" herein includes not only the 22 standard amino acids that are naturally integrated into a peptide but also the D-isomers and modified amino acids. Therefore, in a specific embodiment of the present invention, a peptide herein includes a peptide having D-amino acids. On the other hand, a peptide may include non-standard amino acids such as those that have been post-translationally modified. Examples of post-translational modification include phosphorylation, glycosylation, acylation (including acetylation, myristorylation, plamitoylation), alkylation, carboxylation, hydroxylation, glycation, biotinylation, ubiquitinylation, modification in chemical properties (e.g. β-removing deimidation, deamidation) and structural modification (e.g. formation of disulfide bridge). Also, changes of amino acids include the changes of amino acids that occur due to chemical reaction during the combination process with cross-linkers for formation of a peptide conjugate, such as changes in an amino group, carboxyl group or side chain.

A peptide disclosed herein may be a wild-type peptide that has been identified and isolated from natural sources. On the other hand, when compared to SEQ ID NO: 1 or its fragments, the peptides disclosed herein may be artificial variants that comprise one or more amino acids substituted, deleted and/or inserted. Amino acid alteration in wild-type polypeptides—not only in artificial variants—comprises protein folding and/or conservative substitutions of amino acids that do not influence activities significantly. Examples of conservative substitutions may be within the groups of basic amino acids (arginine, lysine and histidine), acidic amino acids (glutamic acid and aspartic acid), polar amino acids (glutamine and asparagines), hydrophobic amino acids (leucine, isoleucine, valine and methionine), aromatic amino acids (phenylalanine, tryptophan and tyrosine), and small amino acids (glycine, alanine, serine, and threonine). The amino acid substitutions that do not generally alter the specific activities are known in the art. Most common occurring alterations are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, Asp/Gly, and the opposite alterations thereof. Other examples of conservative substitutions are shown in the following table 2.

TABLE 2

| Original amino acid | Examples of residue substitution | Preferable residue substitution |
|---|---|---|
| Ala (A) | val; leu; ile | Val |
| Arg (R) | lys; gln; asn | Lys |
| Asn (N) | gln; his; asp, lys; arg | Gln |
| Asp (D) | glu; asn | Glu |
| Cys (C) | ser; ala | Ser |
| Gln (Q) | asn; glu | Asn |
| Glu (E) | asp; gln | Asp |
| Gly (G) | ala | Ala |
| His (H) | asn; gln; lys; arg | Arg |
| Ile (I) | leu; val; met; ala; phe; norleucine | Leu |
| Leu (L) | norleucine; ile ; val; met; ala; phe | Ile |
| Lys (K) | arg; gln; asn | Arg |
| Met (M) | leu; phe; ile | Leu |
| Phe (F) | leu; val; ile; ala; tyr | Tyr |
| Pro (P) | ala | Ala |
| Ser (S) | thr | Thr |
| Thr (T) | ser | Ser |
| Trp (W) | tyr; phe | Tyr |
| Tyr (Y) | trp; phe ; thr; ser | Phe |
| Val (V) | ile; leu; met; phe; ala; norleucine | Leu |

The substantial modification of the biological properties of peptides are performed by selecting significantly different substitution in the following efficacies: (a) the efficacy in maintaining the structure of the polypeptide backbone in the area of substitution, such as sheet or helical three-dimensional structures, (b) the efficacy in maintaining electrical charge or hydrophobicity of the molecule in a target area, or (c) the efficacy of maintaining the bulk of the side chain. Natural residues are divided into groups by general side chain properties as the following:

(1) hydrophobicity: Norleucine, met, ala, val, leu, ile;
(2) neutral hydrophilicity: cys, ser, thr;
(3) acidity: asp, glu;
(4) basicity: asn, gln, his, lys arg;
(5) residue that affects chain orientation: gly, pro; and
(6) aromaticity: trn, tyr, phe.

Non-conservative substitutions may be performed by exchanging a member of the above classes with that of different classes. Any cysteine residues that are not related to maintaining the proper three-dimensional structure of the peptide can typically be substituted with serine, thus increasing the oxidative stability of the molecule and preventing improper cross-linkage. Conversely, improvement of stability can be achieved by adding cysteine bond(s) to the peptide.

Another type of amino acid variants of peptides are those having a changed pattern of peptide glycosylation. The term "change" herein means deletion of at least one carbohydrate residues that are found in a peptide and/or addition of at least one glycosylated residues that do not exist within a peptide Glycosylation in peptides are typically N-linked or O-linked. The term "N-linked" herein refers to that carbohydrate residues are attached to the side chain of asparagine residues. As tripeptide sequences, asparagine-X-serine and asparagine-X-threonine (wherein the X is any amino acid except proline) are a recognition sequence for attaching a carbohydrate residue enzymatically to the side chain of asparagine. Therefore, with the presence of one of these tripeptide sequences in a polypeptide, the potential glycosylation sites are created. "O-linked glycosylation" means attaching one of sugar N-acetylgalactosamine, galactose, or xylose to hydroxyl amino acids. The hydroxyl amino acids are most typically serine or threonine, but 5-hydroxyproline or 5-hydroxylysine can be used.

Addition of glycosylation site to a peptide is conveniently performed by changing an amino acid sequence to contain the tripeptide sequence mentioned above (for N-linked glycosylation sites). These changes may be made by addition of at least one serine or threonine residues to the first peptide sequence, or by substitution with those residues (for O-linked glycosylation sites).

In the present disclosure, "ischemic injury" refers to a damage occurring as a result of restriction in blood supply and hence shortage of oxygen supply to organs requiring blood supply such as the heart, brain, kidneys, etc., which can lead to dysfunction of tissues and cell death. The cause of an ischemic injury includes vascular disease, coronary thrombosis, cerebrovascular thrombosis, aneurysm rupture, systemic hemorrhage, crush injury, sepsis, severe skin burn, vascular ligation surgery (e.g., spinal ischemia during thoracoabdominal aneurysm surgery), cardiopulmonary bypass, organ transplantation, cardiopulmonary collapse (sudden cardiac death), suffocation, etc., but is not limited thereto.

In the present disclosure, the "ischemic injury" also includes ischemic-reperfusion injury that may occur, for example, during organ transplantation. The ischemic-reperfusion injury includes cerebrovascular ischemic-reperfusion injury, renal ischemic-reperfusion injury, hepatic ischemic-reperfusion injury, ischemic-reperfusion cardiomyopathy, ischemic-reperfusion skin injury, gastrointestinal ischemic-reperfusion injury, intestinal ischemic-reperfusion injury, gastric ischemic-reperfusion injury, ischemic-reperfusion lung injury, pancreatic ischemic-reperfusion injury, ischemic-reperfusion skeletal muscle injury, ischemic-reperfusion abdominal muscle injury, ischemic-reperfusion limb injury, ischemic-reperfusion colitis, mesenteric ischemic-reperfusion injury, asymptomatic ischemic-reperfusion injury, etc., but is not limited thereto.

The ischemic-reperfusion injury can occur frequently during organ transplantation. For example, it is known that gradual functional loss and dysfunction of a transplanted kidney is associated with ischemic-reperfusion injury and the activation of the innate immune system by the ischemic reperfusion tissue injury is one of the important causes.

The peptide having a sequence of SEQ ID NO: 1, the peptide which is a fragment of the peptide having the sequence of SEQ ID NO: 1 or the peptide having 80% or more sequence identity with the peptide according to the present disclosure are advantageous in that they exhibit a high in-vivo stability because of low toxicity. The peptide of SEQ ID NO: 1 is derived from telomerase and consists of 16 amino acids.

The peptide described in SEQ ID NO: 1 is same as the following table 1. The "name" in Table 1 below was used for distinction of peptides. In one aspect, the peptide of SEQ ID NO:1 is the entire peptide of a human telomerase. In a different specific embodiment of the present invention, the peptide having a sequence of SEQ ID NO: 1, the peptide which is a fragment of the peptide having the sequence of SEQ ID NO 1 or the peptide having 80% or more sequence identity with the peptide according to the present disclosure includes "synthetic peptides" synthesized by selecting and synthesizing a peptide corresponding to the pertinent position within the telomerase. SEQ ID NO: 2 is the amino acid sequence of the entire telomerase.

TABLE 1

| SEQ ID No. | Name | POSITION IN TELOMERASE | SEQUENCE | LENGTH |
|---|---|---|---|---|
| 1. | pep1 | [611-626] | EARPALLTSRLRFIPK | 16 aa |
| 2. | Telomerase | [1-1132] | MPRAPRCRAVRSLLRSHYRE VLPLATFVRRLGPQGWRLVQ RGDPAAFRALVAQCLVCVP WDARPPPAAPSFRQVSCLKE LVARVLQRLCERGAKNVLAF GFALLDGARGGPPEAFTTSV RSYLPNTVTDALRGSGAWGL LLRRVGDDVLVHLLARCALF VLVAPSCAYQVCGPPLYQLG AATQARPPPHASGPRRRLGC ERAWNHSVREAGVPLGLPAP GARRRGGSASRSLPLPKRPRR GAAPEPERTPVGQGSWAHPG RTRGPSDRGFCVVSPARPAEE ATSLEGALSGTRHSHPSVGR QHHAGPPSTSRPPRPWDTPCP PVYAETKHFLYSSGDKEQLR PSFLLSSLRPSLTGARRLVETI FLGSRPWMPGTPRRLPRLPQ RYWQMRPLFLELLGNHAQC PYGVLLKTHCPLRAAVTPAA GVCAREKPQGSVAAPEEEDT DPRRLVQLLRQHSSPWQVYG FVRACLRRLVPPGLWGSRHN ERRFLRNTKKFISLGKHAKLS LQELTW KMSVRDCAWLRRSPGVGCV PAAEHRLREEILAKFLHWLM SVYVVELLRSFFYVTETTFQK NRLFFYRKSVWSKLQSIGIRQ HLKRVQLRELSEAEVRQHRE ARPALLTSRLRFIPKPDGLRPI VNMDYVVGARTFRREKRAE RLTSRVKALFSVLNYERARR PGLLGASVLGLDDIHRAWRT FVLRVRAQDPPPELYFVKVD VTGAYDTIPQDRLTEVIASIIK PQNTYCVRRYAVVQKAAHG HVRKAFKSHVSTLTDLQPYM RQFVAHLQETSPLRDAVVIE QSSSLNEASSGLFDVFLRFMC HHAVRIRGKSYVQCQGIPQG SILSTLLCSLCYGDMENKLFA GIRRDGLLLRLVDDFLLVTPH LTHAKTFLRTLVRGVPEYGC VVNLRKTVVNFPVEDEALGG TAFVQMPAHGLFPWCGLLLD TRTLEVQSDYSSYARTSIRAS LTFNRGFKAGRNMRRKLFGV LRLKCHSLFLDLQ VNSLQTVCTNIYKILLLQAYR FHACVLQLPFHQQVWKNPTF FLRVISDTASLCYSILKAKNA | 1132 aa |

TABLE 1-continued

| SEQ ID No. | Name | POSITION IN TELOMERASE | SEQUENCE | LENGTH |
|---|---|---|---|---|
| | | | GMSLGAKGAAGPLPSEAVQ WLCHQAFLLKLTRHRVTYVP LLGSLRTAQTQLSRKLPGTTL TALEAAANPALPSDFKTILD | |

In an aspect, the present disclosure provides a composition for treating and preventing an ischemic injury, containing a peptide comprising an amino acid sequence of SEQ ID NO: 1, a peptide having 80% or more sequence identity with the amino acid sequence or a peptide which is a fragment thereof as an active ingredient.

In one embodiment of the present invention, the composition may contain 0.1 µg/mg to 1 mg/mg, specifically 1 µg/mg to 0.5 mg/mg, more specifically 10 µg/mg to 0.1 mg/mg of a peptide comprising amino acid sequence of at least one of SEQ ID NO: 1, a peptide comprising a amino acid sequence at least 80% sequence homology with the above-mentioned sequences, or a fragment of the above-mentioned peptides. When the peptide is contained in the above-mentioned ranges, both of safety and stability of the composition can be satisfied and the ranges are appropriate in terms of cost-effectiveness.

In one embodiment of the present invention, the composition may have applications with all animals including human, dog, chicken, pig, cow, sheep, guinea pig, and monkey.

In an exemplary embodiment, the present disclosure provides a pharmaceutical composition for treating and preventing ischemic-reperfusion injury, containing a peptide comprising an amino acid sequence of SEQ ID NO: 1, a peptide having 80% or more sequence identity with the amino acid sequence or a peptide which is a fragment thereof as an active ingredient.

In one embodiment of the present invention, the pharmaceutical composition may be administered through oral, rectal, transdermal, intravenous, intramuscular, intraperitoneal, in the bone marrow, epidural or subcutaneous routes.

Forms of oral administration may be, but not limited to, tablets, pills, soft or hard capsules, granules, powders, solution, or emulsion. Forms of non-oral administration can be, but not limited to, injections, drips, lotions, ointments, gels, creams, suspensions, emulsions, suppository, patch, or spray.

In one embodiment of the present invention, the pharmaceutical composition, if necessary, may contain additives, such as diluents, excipients, lubricants, binders, disintegrants, buffers, dispersants, surfactants, coloring agents, aromatics or sweeteners. In one embodiment of the present invention, the pharmaceutical composition may be manufactured by conventional methods of the industry in the art.

In one embodiment of the present invention, the dose of the active ingredient of the medical composition may vary according to the patient's age, sex, weight, pathology and state, administration route, or prescriber's judgment. Dosage based on these factors may be determined within levels of those skilled in the art, and the daily dose, for example, may be, but not limited to, 0.1 µg/kg/day to 1 g/kg/day, specifically 1 µg/kg/day to 10 mg/kg/day, more specifically the 10 µg/kg/day to 1 mg/kg/day, more specifically the 50 µg/kg/day to 100 µg/kg/day. In one embodiment of the present invention, the pharmaceutical composition may be administered, but not limited to, 1 to 3 times a day.

In an exemplary embodiment, the present disclosure provides a food composition for treating and preventing ischemic-reperfusion injury, containing a peptide comprising an amino acid sequence of SEQ ID NO: 1, a peptide having 80% or more sequence identity with the amino acid sequence or a peptide which is a fragment thereof as an active ingredient.

In one embodiment of the present invention, food composition is not limited to specific forms, but, for example, may be tablets, granules, powder, liquid, and solid forms. Each form may be formed with ingredients commonly used in the industry appropriately chosen by those skilled in the art, in addition to the active ingredient, and may produce a synergic effect in combination of other ingredients.

Decision for dosage on the above-mentioned active ingredient is within the level of those skilled in the art, and daily dosage, for example, may be 1 µg/kg/day to 10 mg/kg/day, more specifically the 10 µg/kg/day to 1 mg/kg/day, more specifically the 50 µg/kg/day to 100 µg/kg/day, but not limited to these numbers and can vary according to age, health status, complications and other various factors.

The terms used herein is intended to be used to describe the embodiments, not to limit the present invention. Terms without numbers in front are not to limit the quantity but to show that there may be more than one thing of the term used. The terms "comprising", "having", "including" and "containing" shall be interpreted openly (i.e. "including but not limited to").

Mention of a numerical range is used instead of stating separate numbers within the range, so unless it is explicitly stated, the range should be construed as if all the numbers within the range are separately described herein. The end values of all the ranges are included in the range and can be combined independently.

Unless otherwise noted or clearly contradicting in context, all methods mentioned herein can be performed in a proper order. The use of any one embodiment and all embodiment, or exemplary language (e.g., "such as", "like"), unless included in the claims, is used to more clearly describe the present invention, not to limit the scope of the present invention. Any language herein outside of the claims should not be interpreted as a necessity of the present invention. Unless defined otherwise, technical and scientific terms used herein have meanings ordinarily understood by a person skilled in the art that the present invention belongs to.

The preferred embodiments of the present invention include the best mode known to the inventors to perform the present invention. Variations in the preferred embodiments can become clear to those skilled in the art after reading the statements above. The present inventors hope that those skilled in the art can use the variations adequately and present invention be conducted in other ways than listed herein. Thus, the present invention, as allowed by the patent law, includes equivalents, modifications and variations thereof, of the key points of the invention stated in the appended claims. In addition, all possible variations within any combination of the above-mentioned components are included in the present invention, unless explicitly stated otherwise or contradicting in context. Although the present invention is described and shown by exemplary embodiments, those skilled in the art will understand well that there can be various changes in the form and details without departing from the spirit of the invention and range, defined by the claims below.

In the following examples, the effect of a peptide having a sequence of SEQ ID NO: 1 (PEP 1) of preventing and treating an ischemic injury was investigated by administering the peptide to ischemic-reperfusion injury portions induced by renal and rectus abdominis myocutaneous flaps and confirming the effect of inhibiting renal injury and improving flap survivability.

Hereinafter, the present disclosure will be described in detail through examples and test examples. However, the following examples and test examples are for illustrative purposes only and it will be apparent to those of ordinary skill in the art that the scope of the present disclosure is not limited by the examples and test examples.

MODE FOR INVENTION

Example 1: Synthesis of Peptide

The peptide of SEQ ID NO: 1 was synthesized according to the conventionally known method of solid phase peptide synthesis. More specifically, the peptide was synthesized by coupling each amino acid from C-terminus through Fmoc solid phase peptide synthesis, SPPS, using ASP48S (Peptron, Inc., Daejeon ROK). Those peptides with their first amino acid at the C-terminus being attached to a resin were used as follows:

$NH_2$-Lys(Boc)-2-chloro-Trityl Resin
$NH_2$-Ala-2-chloro-Trityl Resin
$NH_2$-Arg(Pbf)-2-chloro-Trityl Resin All the amino acids to synthesize the peptide were protected by Fmoc at the N-terminus, and the amino acid residues were protected by Trt, Boc, t-Bu (t-butylester), Pbf (2,2,4,6,7-pentamethyl dihydro-benzofuran-5-sulfonyl) that can be dissolved in an acid. Examples include the followings:

Fmoc-Ala-OH, Fmoc-Arg(Pbf)-OH, Fmoc-Glu(OtBu)-OH, Fmoc-Pro-OH, Fmoc-Leu-OH, Fmoc-Ile-OH, Fmoc-Phe-OH, Fmoc-Ser(tBu)-OH, Fmoc-Thr(tBu)-OH, Fmoc-Lys(Boc)-OH, Fmoc-Gln(Trt)-OH, Fmoc-Trp(Boc)-OH, Fmoc-Met-OH, Fmoc-Asn(Trt)-OH, Fmoc-Tyr(tBu)-OH, Fmoc-Ahx-OH, Trt-Mercaptoacetic acid.

HBTU[2-(1H-Benzotriazole-1-yl)-1,1,3,3-tetramethylaminium hexafluorophosphate]/HOBt[N-Hydroxybenzotriazole]/NMM[4-Methylmorpholine] were used as the coupling reagents. Piperidine in 20% DMF was used to remove Fmoc. In order to remove the protection from residues or to separate the synthesized peptides from Resin, cleavage cocktail [TFA (trifluoroacetic acid)/TIS (triisopropylsilane)/EDT (ethanedithiol)/$H_2O$=92.5/2.5/2.5/2.5] was used.

The peptide synthesis was performed by using solid phase scaffold with the repetition of the following processes: starting with the amino acid protection, separate reaction of each amino acid, washing with solvents, and deprotection. Each peptide was synthesized by using the solid phase scaffold combined to starting amino acid with the amino acid protection, reacting the corresponding amino acids separately, washing with a solvent and deprotected, and repeating the processes. Upon the release from the resin, the synthesized peptides were purified by HPLC, validated by Mass Spectrometry, and freeze-dried, and verify for synthesis by MS, and then freeze-dried.

The purity of the prepared peptide was found to be 95% or higher by high-performance liquid chromatography.

A specific peptide synthesis process is described as the following based on the synthesis process of PEP 1 which has SEQ ID NO: 1.

1) Coupling

The amino acid (8 equivalent) protected with $NH_2$-Lys (Boc)-2-chloro-Trityl Resin, and coupling agent HBTU(8 equivalent)/HOBt(8 equivalent)/NMM(16 equivalent) melted in DMF were mixed together, and incubated at room temperature (RT) for 2 hr. Following the incubation, the reaction mixture was subjected to the sequential washes of DMF, MeOH, and DMF.

2) Fmoc Deprotection

Piperidine in 20% DMF was added and incubated at RT for 5 minutes 2 times, then sequentially washed with DMF, MeOH, and DMF.

3) Making the basic framework of peptide, $NH_2$-E(OtBu)-A-R(Pbf)-P-A-L-L-T(tBu)-S(tBu)-R(Pbf)L-R(Pbf)-F-I-P-K (Boc)-2-chloro-Trityl Resin) by repeating the above mentioned reactions 1) and 2).

4) Cleavage: Cleavage Cocktail was added to the completely synthesized peptide, thus separating the synthesized peptide from the resin.

5) Pre-chilled diethyl ether was added into the obtained mixture, and then centrifugation was used to precipitate gathered peptide.

6) After purification by Prep-HPLC, the molecular weight was confirmed by LC/MS and lyophilized to produce in a powder form.

Example 2: Confirmation of PEP1's Effect of Inhibiting Renal Injury in Renal Ischemic-Reperfusion Injury Model Test Example 1: Induction of Ischemic Reperfusion A renal ischemic-reperfusion injury mouse model was established by inducing ischemic reperfusion by bilaterally clamping renal pedicles for 30 minutes and restoring blood flow 30 minutes later by removing the clamps. Test groups were divided into an administered group (PEP 1), a control group (PBS without PEP 1), and a sham group (no bilateral clamping). PEP 1 was subcutaneously injected at a concentration of 1000 nmol/kg 30 minutes before and 12 hours after the induction of ischemic reperfusion.

C57BL/6 mouse (8 weeks old; Charles River Laboratories, Wilmington, Mass.) was used to induce renal ischemic-reperfusion injury. After blocking blood flow by clamping the renal pedicles with vascular forceps and inducing ischemia for 28 minutes, reperfusion was performed.

The peptide PEP 1 was diluted in PBS to a concentration of 1000 nmol/kg and intraperitoneally (i.p.) injected twice 30 minutes before and 12 hours after the ischemic reperfusion. The test was conducted for the administered group (PEP 1), the control group (PBS), and the sham group (no ischemic reperfusion).

Test Example 2: PEP 1's Effect of Preventing IRI-Induced Renal Failure

Blood was taken 24 hours after the ischemic reperfusion and the levels of blood urea nitrogen (BUN) and creatine as renal toxicity markers were measured. Renal tissue was taken and prepared into paraffin blocks for immunohistochemical and histological studies. Then, proteins were extracted and the levels of cytokines were measured. The concentrations of creatine and BUN were measured using an autoanalyzer (Technicon RA-1000; Bayer, Tarrytown, N.Y.).

As a result, the PEP 1-administered group showed significantly decreased BUN and creatine levels as compared to the PBS control group (FIG. 1).

Test Example 3: PEP 1's Effect of Preventing Renal Tissue Injury

Figure 2:
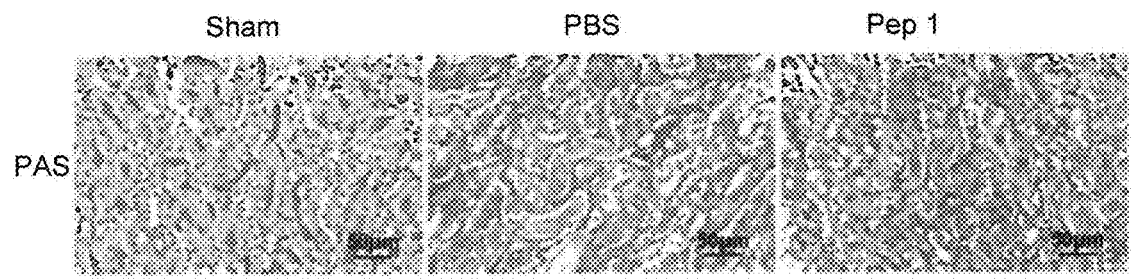
FIG. 2 shows a result of staining renal tissue with periodic acid-Schiff (PAS) stain 24 hours after ischemic reperfusion.
Figure 3:
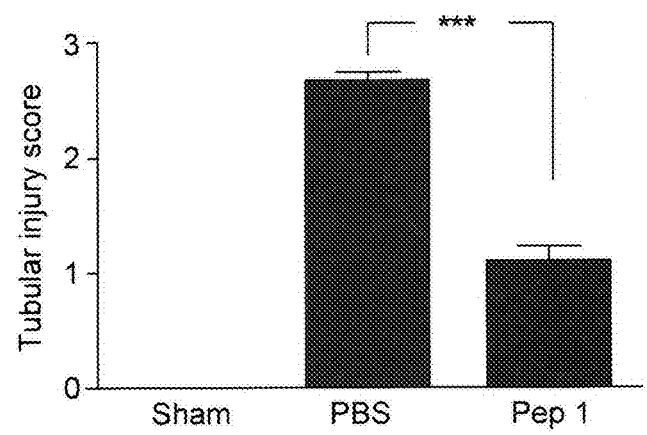
FIG. 3 shows a result of conducting renal tissue injury scoring 24 hours after ischemic reperfusion.

Renal tissue was stained with periodic acid-Schiff (PAS) stain according to the protocol of the manufacturer (Polysciences, Inc., Warrington, Pa., USA) 24 hours after the ischemic reperfusion. After the staining, renal tissue injury was evaluated through renal tissue injury scoring. The PEP 1-administered group showed remarkably decreased renal tissue injury as compared to the PBS control group (FIG. 2 and FIG. 3).

Test Example 4: Effect of Inhibiting Renal Apoptosis

Renal apoptosis was evaluated by staining renal tissue with TUNEL stain 24 hours after the ischemic reperfusion. Renal paraffin sections were stained with TUNEL using a TUNEL staining kit (Roche Applied Science, Indianapolis, Ind., USA).

Figure 4:
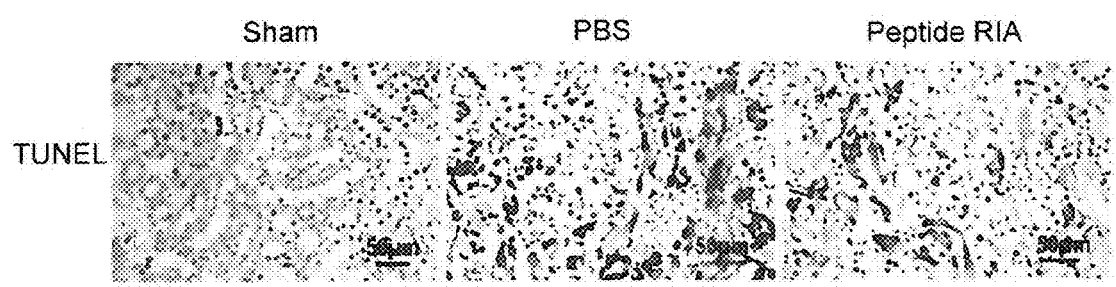
FIG. 4 shows a result of staining renal tissue with TUNEL stain 24 hours after ischemic reperfusion.
Figure 5:
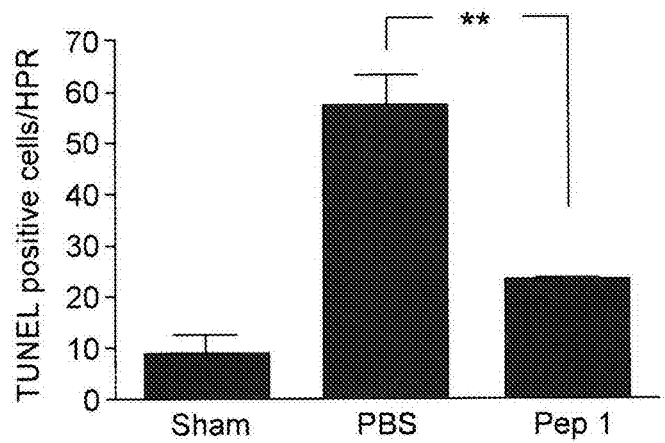
FIG. 5 shows a result of measuring TUNEL-positive cells stained with TUNEL stain 24 hours after ischemic reperfusion.

As a result, the PEP 1-administered group showed remarkably decreased TUNEL-positive cells as compared to the PBS control group, indicating that PEP 1 inhibits the cell death of the renal tissue (FIG. 4 and FIG. 5).

Test Example 5: Effect of Inhibiting Filtration of Innate Immune Cells in Renal Tissue Infiltration of innate immune cells was evaluated by immnohistologically staining renal tissue with F4/80 (macrophage maker) and Gr-1 (neutrophil maker) 24 hours after the ischemic reperfusion. Specifically, macrophage-specific antibody (F4/80; Abcam, Cambridge, Mass.) was used to immunochemically stain infiltrating macrophages and neutrophils in paraffin sections.

Figure 6:
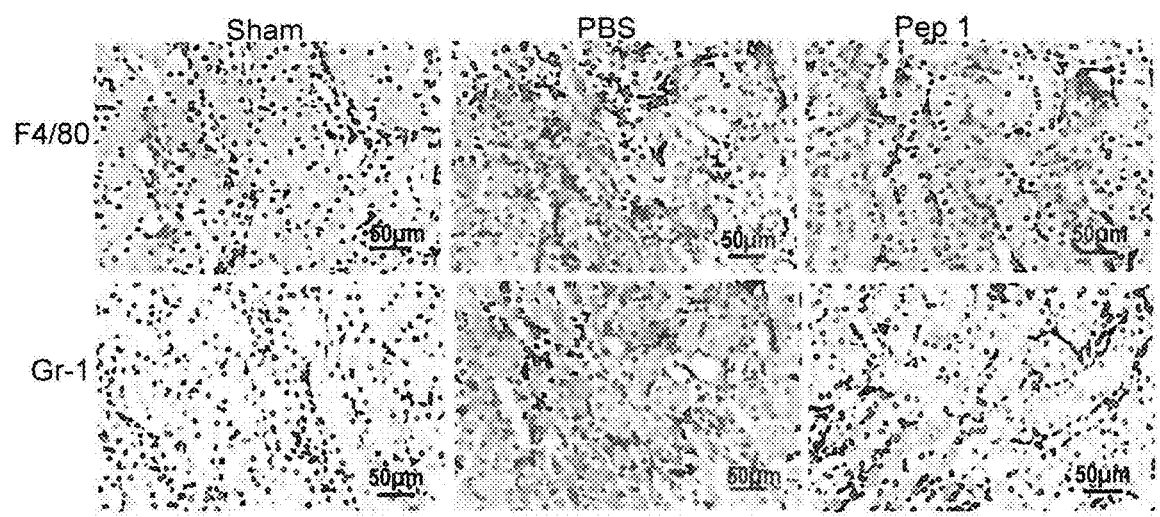
FIG. 6 shows a result of evaluating infiltration of innate immune cells by immunohistologically staining renal tissue with F4/80 (macrophage maker) and Gr-1 (neutrophil maker) 24 hours after ischemic reperfusion.
Figure 7:
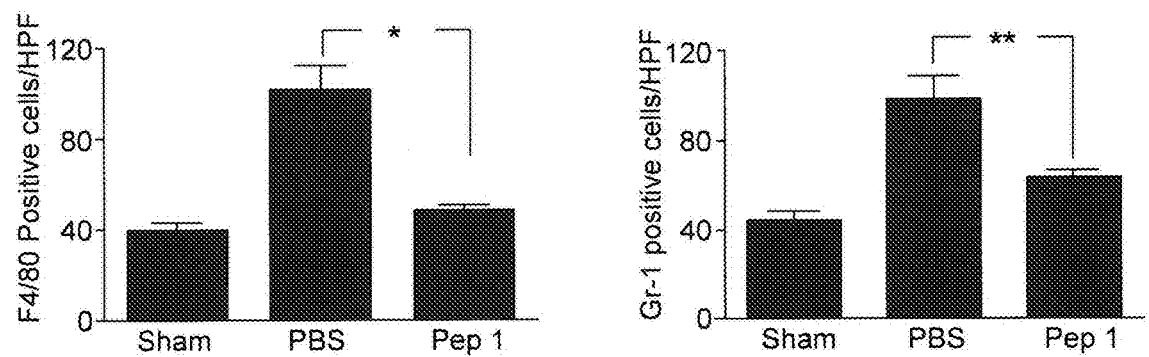
FIG. 7 shows a result of measuring F4/80 (macrophage maker)- and Gr-1 (neutrophil maker)-positive cells in renal tissue 24 hours after ischemic reperfusion.

The PEP 1-administered group showed remarkably decreased infiltration of macrophages and neutrophils into renal tissue as compared to the PBS control group (FIG. 6 and FIG. 7).

Test Example 6: Effect of Inhibiting Secretion of Inflammatory Cytokines

Protein was extracted from renal tissue 24 hours after the ischemic reperfusion and the levels of IL-6, MCP-1 and TNF-α were measured according to the cytometric bead array method. Mouse IL-6, MCP-1, TNF-α ELISA kits were purchased from R&D Systems and the test was conducted according to the manufacturer's protocol.

Figure 8:
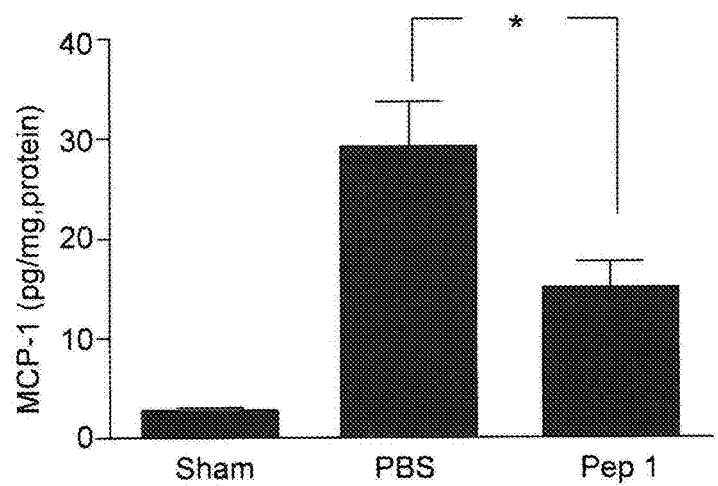
FIGS. 8-10 show inhibited secretion of inflammatory cytokines in renal tissue 24 hours after ischemic reperfusion.
Figure 9:
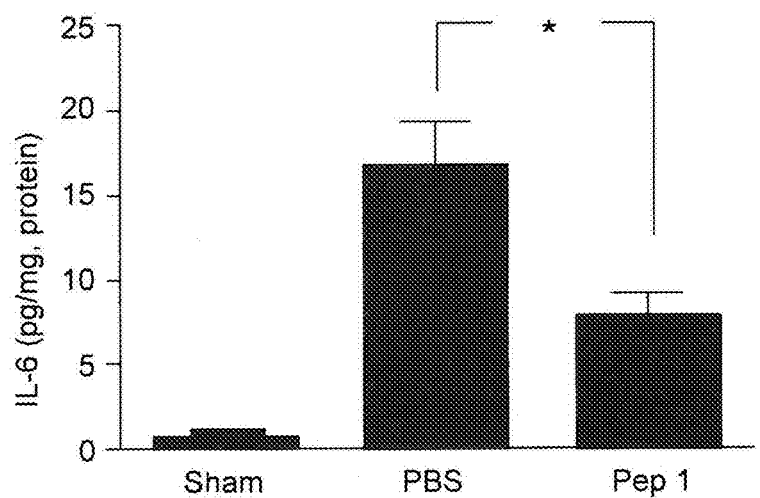
Figure 10:
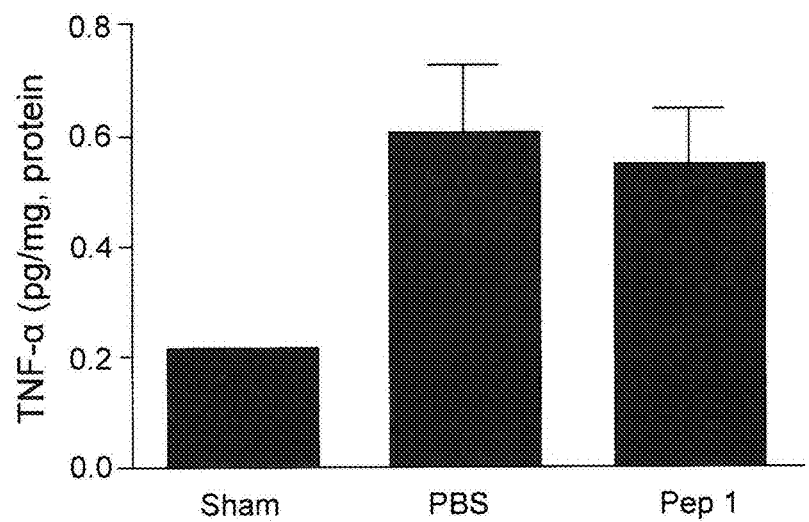

As a result, the PEP 1-administered group showed significantly decreased IL-6 and MCP-1 levels as compared to PBS control group, whereas no significant difference was observed for TNF-α (FIGS. 8-10).

As described above, the PEP 1's effect of preventing renal ischemic-reperfusion injury was evaluated by testing renal failure (BUN and creatine), renal tissue injury (tubular injury), renal apoptosis, immune cell infiltration and secretion of cytokines in renal tissue.

The PBS control group showed increased serum BUN and creatine levels and increased renal tissue injury as compared to the sham group. In contrast, the PEP 1-administered group showed significantly decreased BUN and creatine levels and decreased renal tissue injury and renal apoptosis as compared to the control group. Also, the PEP 1-administered group showed inhibited infiltration of inflammatory cells (neutrophils and macrophages) and significantly inhibited secretion of inflammatory cytokines (interleukin-6 and monocyte chemotactic protein-1) in the kidneys as compared to the PBS control group.

Figure 11:
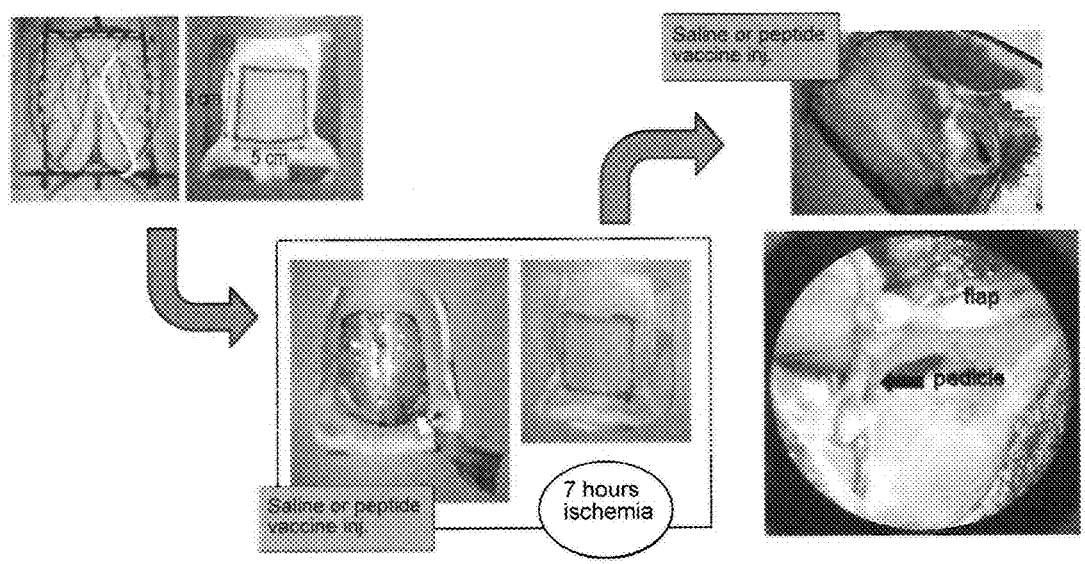
FIG. 11 shows a procedure of inducing ischemic-reperfusion injury for evaluation of a flap survival rate.

Example 3: PEP 1's Effect of Improving Rectus Abdominis Myocutaneous Flap Survivability in Ischemic-Reperfusion Injury Model Test Example 1: Induction of Ischemic Reperfusion A rat model of ischemic-reperfusion injury was established by acquiring 5 cm×5 cm skin flaps from the abdomen of Sprague-Dawley rats (weighing 180-230 g), administering PEP1 or saline, inducing local ischemia through clamping and then restoring blood flow 7 hours later by removing the clamps (see FIG. 11).

Test groups were divided into an administered group (PEP 1), a control group (PBS without PEP 1), and a sham group (no ischemic-reperfusion injury induced). PEP 1 (10 mg/500 μL) or PBS (500 μL) was intramuscularly injected 30 minutes before and 1, 2, 3, 4, 5 and 7 days after the induction of ischemic reperfusion.

Test Example 2: PEP1's Effect of Improving Flap Survivability

Flap survivability was measured 7 days after the induction of ischemic reperfusion. The flap survival rate was measured through analysis of digital images using the imageJ program.

Figure 12:
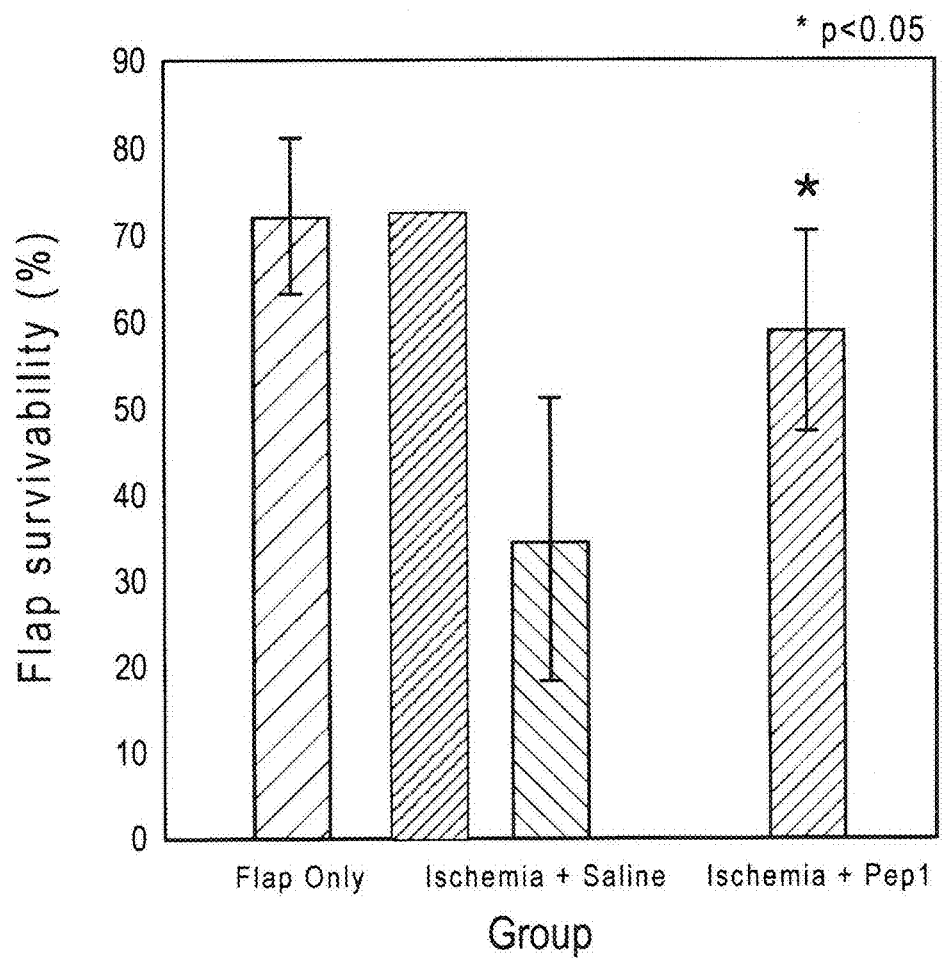
FIG. 12 shows a result of measuring the flap survival rates of a PEP1-treated group and a saline-treated group 7 days after induction of ischemic reperfusion.
Figure 13:
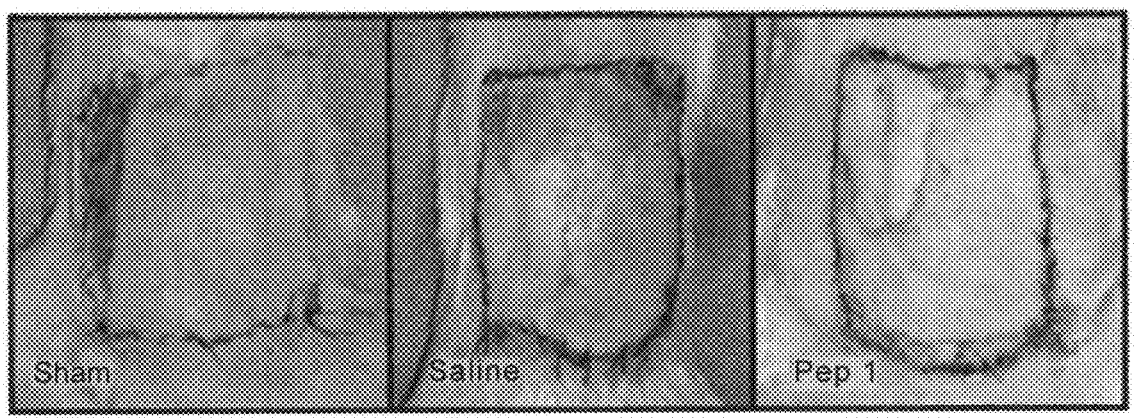
FIG. 13 shows digital images obtained using the ImageJ program.

As a result, the flap survival rate of the PBS-treated group was 34.69%±16.44% and the PEP1-treated group showed improved flap survival rate of 58.88%±11.44% (see FIG. 12). A statistical significance (p<0.05) was found between the groups.

What is claimed is:

1. A method of treating an ischemic injury, comprising: administering to a subject with an ischemic injury an effective dose of an isolated telomerase peptide consisting of the amino acid sequence of SEQ ID NO: 1, wherein the administration decreases the ischemic injury.

2. The method of claim 1, wherein the ischemic injury is selected from the group consisting of ischemic-reperfusion injury, vascular disease, coronary thrombosis, cerebrovascular thrombosis, aneurysm rupture, systemic hemorrhage, crush injury, sepsis, vascular ligation surgery, cardiopulmonary bypass, organ transplantation, injury caused by cardiopulmonary collapse and injury caused by suffocation.

3. The method of claim 1, wherein the peptide is administered in a single dose at a concentration of 0.1 μg/kg to 1.0 g/kg.

4. The method of claim 1, wherein the peptide is administered in a single dose at a concentration of 1 μg/kg to 10 mg/kg.

5. The method of claim 1, wherein the peptide is administered 1 to 3 times a day.

6. The method of claim 5, wherein the peptide is administered at a daily dose of 0.1 µg/kg to 1.0 g/kg.

7. The method of claim 6, wherein the peptide is administered 1 to 3 times daily.

8. A method of treating an ischemic injury, comprising: administering to a subject with an ischemic injury an effective dose of a composition comprising an isolated telomerase peptide consisting of the amino acid sequence of SEQ ID NO: 1, wherein the administration decreases the ischemic injury.

9. The method of claim 8, wherein the ischemic injury is selected from the group consisting of ischemic-reperfusion injury, vascular disease, coronary thrombosis, cerebrovascular thrombosis, aneurysm rupture, systemic hemorrhage, crush injury, sepsis, vascular ligation surgery, cardiopulmonary bypass, organ transplantation, injury caused by cardiopulmonary collapse and injury caused by suffocation.

10. The method of claim 8, wherein the composition is administered through oral, rectal, transdermal, intravenous, intramuscular, intraperitoneal, in the bone marrow, epidural, or subcutaneous routes.

11. The method of claim 8, wherein the composition comprises 0.1 µg/mg to 1 mg/mg of isolated peptide.

12. The method of claim 8, wherein the peptide is administered in a single dose at a concentration of 0.1 µg/kg to 1.0 g/kg.

13. The method of claim 8, wherein the peptide is administered in a single dose at a concentration of 1 µg/kg to 10 mg/kg.

14. The method of claim 8, wherein the peptide is administered 1 to 3 times a day.

15. The method of claim 14, wherein the peptide is administered at a daily dose of 0.1 µg/kg to 1.0 g/kg.

16. The method of claim 15, wherein the peptide is administered 1 to 3 times daily.

* * * * *